US012156898B2

(12) United States Patent
Markham et al.

(10) Patent No.: US 12,156,898 B2
(45) Date of Patent: Dec. 3, 2024

(54) FORMULATIONS OF TERLIPRESSIN

(71) Applicant: BIOVIE Inc., Santa Monica, CA (US)

(72) Inventors: Penelope Markham, Clifton, VA (US); Jonathan Adams, Chicago, IL (US); Denise Smith, Clinton, OH (US); Jorge Bacardit Cabado, Girona (ES)

(73) Assignee: BioVie, Inc., Los Angeles, CA (US)

( * ) Notice: Subject to any disclaimer, the term of this patent is extended or adjusted under 35 U.S.C. 154(b) by 335 days.

(21) Appl. No.: 17/611,478

(22) PCT Filed: May 22, 2020

(86) PCT No.: PCT/US2020/034269
§ 371 (c)(1),
(2) Date: Nov. 15, 2021

(87) PCT Pub. No.: WO2020/237170
PCT Pub. Date: Nov. 26, 2020

(65) Prior Publication Data
US 2022/0233634 A1    Jul. 28, 2022

Related U.S. Application Data

(60) Provisional application No. 62/851,366, filed on May 22, 2019.

(51) Int. Cl.
| | | |
|---|---|---|
| *A61K 38/095* | (2019.01) | |
| *A61K 9/00* | (2006.01) | |
| *A61K 9/08* | (2006.01) | |
| *A61K 38/12* | (2006.01) | |
| *A61K 38/22* | (2006.01) | |
| *A61K 47/02* | (2006.01) | |
| *A61K 47/12* | (2006.01) | |
| *A61K 47/18* | (2017.01) | |
| *A61M 5/00* | (2006.01) | |
| *A61M 5/178* | (2006.01) | |
| *A61M 5/142* | (2006.01) | |

(52) U.S. Cl.
CPC .......... *A61K 38/095* (2019.01); *A61K 9/0019* (2013.01); *A61K 9/08* (2013.01); *A61K 38/12* (2013.01); *A61K 38/2278* (2013.01); *A61K 47/02* (2013.01); *A61K 47/12* (2013.01); *A61K 47/183* (2013.01); *A61M 5/002* (2013.01); *A61M 5/178* (2013.01); *A61M 5/14248* (2013.01)

(58) Field of Classification Search
CPC ........ A61K 38/095; A61K 9/08; A61K 47/12; A61M 5/178
See application file for complete search history.

(56) References Cited

U.S. PATENT DOCUMENTS

| | | | |
|---|---|---|---|
| 5,482,931 A | 1/1996 | Harris et al. | |
| 7,160,853 B2 | 1/2007 | Lebrec et al. | |
| 2003/0119728 A1 | 6/2003 | Scheidl et al. | |
| 2004/0022792 A1* | 2/2004 | Klinke | A61K 47/183 514/8.1 |
| 2004/0102362 A1 | 5/2004 | Lebrec et al. | |
| 2004/0153032 A1* | 8/2004 | Garribotto | A61M 5/14248 604/131 |
| 2009/0305959 A1 | 12/2009 | Laporte et al. | |
| 2010/0203014 A1 | 8/2010 | Maggio | |
| 2010/0311642 A1 | 12/2010 | Riviere et al. | |
| 2010/0331653 A1* | 12/2010 | Stafford | G01N 33/48785 436/95 |
| 2011/0003890 A1 | 1/2011 | Schwartz et al. | |
| 2011/0237494 A1 | 9/2011 | Laporte et al. | |
| 2011/0300109 A1 | 12/2011 | Tepic et al. | |
| 2012/0157526 A1 | 6/2012 | Jalan et al. | |
| 2013/0197044 A1 | 8/2013 | Pavliv et al. | |
| 2014/0147875 A1 | 5/2014 | Everson et al. | |
| 2014/0329747 A1 | 11/2014 | Tidmarsh | |
| 2014/0378660 A1 | 12/2014 | Short et al. | |
| 2015/0056194 A1 | 2/2015 | Hsu | |
| 2015/0126432 A1 | 5/2015 | Wisniewski et al. | |
| 2016/0113994 A1 | 4/2016 | Jamil et al. | |
| 2019/0328831 A1 | 10/2019 | Jamil et al. | |
| 2020/0046798 A1 | 2/2020 | Jamil et al. | |
| 2020/0237856 A1 | 7/2020 | Jamil et al. | |
| 2020/0246418 A1 | 8/2020 | Jamil et al. | |
| 2021/0085751 A1 | 3/2021 | Jezek et al. | |
| 2022/0080023 A1 | 3/2022 | Jezek et al. | |

FOREIGN PATENT DOCUMENTS

| | | | |
|---|---|---|---|
| CN | 102440957 A | 5/2012 | |
| CN | 108659104 A | 10/2018 | |
| CN | 109010795 A | 10/2021 | |
| EP | 2326341 B1 | 7/2012 | |
| EP | 2185170 B1 | 4/2017 | |
| WO | 2002/076495 A1 | 10/2002 | |

(Continued)

OTHER PUBLICATIONS

Petitioner's Request for Oral Argument. Paper 24 in *Mallinckrodt* v. *BioVie* IPR2018-00974, filed by Mallinckrodt on Jul. 15, 2019, pp. 1-5.

(Continued)

*Primary Examiner* — Gyan Chandra

(74) *Attorney, Agent, or Firm* — McDonnell Boehnen Hulbert & Berghoff LLP

(57) ABSTRACT

The disclosure provides pharmaceutical compositions comprising terlipressin having increased concentration with long term storage stability.

18 Claims, 5 Drawing Sheets

(56) References Cited

FOREIGN PATENT DOCUMENTS

| | | | |
|---|---|---|---|
| WO | 2003/105767 | A2 | 12/2003 |
| WO | 2006/083689 | A2 | 8/2006 |
| WO | 2006/138181 | A2 | 12/2006 |
| WO | 2008/084237 | A2 | 7/2008 |
| WO | 2008/150305 | A1 | 12/2008 |
| WO | 2009/073569 | A2 | 6/2009 |
| WO | 2010/033220 | A2 | 3/2010 |
| WO | 2010/048183 | A1 | 4/2010 |
| WO | 2012/042371 | A2 | 4/2012 |
| WO | 2013/106072 | A1 | 7/2013 |
| WO | 2015/175668 | A1 | 11/2015 |
| WO | 2017/150824 | A1 | 9/2017 |
| WO | 2019/239386 | A1 | 12/2019 |

OTHER PUBLICATIONS

Petitioner's Sur-Reply to Patent Owner's Reply in Support of Its Contingent Motion to Amend. Paper 25 in *Mallinckrodt v. BioVie* IPR2018-00974, filed by Mallinckrodt on Jul. 15, 2019, pp. 1-18.
United States Patent and Trademark Office. Order, Conduct of the Proceeding, 37 C.F.R. § 42.5, dated Jul. 16, 2019. Paper 26 in *Mallinckrodt v. BioVie* IPR2018-00974, pp. 1-3.
United States Patent and Trademark Office. Order, Oral Hearing, 37 C.F.R. § 42.70, dated Jul. 17, 2019. Paper 27 in *Mallinckrodt v. BioVie* IPR2018-00974, pp. 1-6.
Petitioner's Motion to Strike Portions of Patent Owner's Sur-Reply. Paper 28 in *Mallinckrodt v. BioVie* IPR2018-00974, filed by Mallinckrodt on Jul. 22, 2019, pp. 1-4.
Patent Owner's Opposition to Petitioner's Motion to Strike Portions of Patent Owner's Sur-Reply. Paper 29 in *Mallinckrodt v. BioVie* IPR2018-00974, filed by BioVie on Jul. 29, 2019, pp. 1-8.
United States Patent and Trademark Office. Record of Oral Hearing held on Aug. 12, 2019. Paper 30 in *Mallinckrodt v. BioVie* IPR2018-00974, issued on Sep. 4, 2019, pp. 1-73.
United States Patent and Trademark Office. Order, Conduct of the Proceeding, 37 C.F.R. § 42.5, dated Oct. 11, 2019. Paper 31 in *Mallinckrodt v. BioVie* IPR2018-00974, pp. 1-3.
Patent Owner's Notice of Supplemental Authority. Paper 32 in *Mallinckrodt v. BioVie* IPR2018-00974, filed by BioVie on Oct. 16, 2019, pp. 1-5.
Petitioner's Reply to Patent Owner's Notice of Supplemental Authority. Paper 33 in *Mallinckrodt v. BioVie* PR2018-00974, filed by Mallinckrodt on Oct. 21, 2019, pp. 1-5.
United States Patent and Trademark Office. Final Written Decision, dated Nov. 13, 2019. Paper 34 in *Mallinckrodt v. BioVie* IPR2018-00974, pp. 1-77.
Petitioner Email to the Board dated Jul. 12, 2019. Exhibit 3001 in *Mallinckrodt v. BioVie* IPR2018-00974, 1 page.
Patent Owner Email to the Board dated Oct. 10, 2019. Ex. 3002 in *Mallinckrodt v. BioVie* IPR2018-00974, 1 page.
https://en.wikipedia.org/w/index.php?title=Infusion_pump&oldid=855450445 'Infusion Pump' Aug. 18, 2018, pp. 1-3.
https://en.wikipedia.org/w/index.php?title=Intravenous_therapy&oldid=892779562 'Intravenous therapy' Apr. 16, 2019, pp. 1-15.
Terlipressin acetate EVER Pharma 0.2 mg/ml solution for injection Summary of Product Characteristics. Oct. 28, 2016, pp. 1-12.
Glypressin 1 mg powder and solvent for solution for injection Summary of Product Characteristics. Aug. 2017, pp. 1-5.
International Search Report and Written Opinion for International Application No. PCT/US2020/034269, mailed Aug. 25, 2020.
Alessandria et al., "Noradrenalin vs terlipressin in patients with hepatorenal syndrome: A prospective, randomized, unblinded, pilot study," Journal of Hepatology, 47:499-505 (2007).
Alessandria et al., "Renal failure in cirrhotic patients: role of terlipressin in clinical approach to hepatorenal syndrome type 2," European Journal of Gastroenterology & Hepatology, 14:1363-1368 (2002).

Alessandria et al., "MELD Score and Clinical Type Predict Prognosis in Hepatorenal Syndrome: Relevance to Liver Transplantation," Hepatology, 41:1282-89 (2005).
Ali et al., "Clinical Study on the Therapeutic Role of Midodrine in Non azotemic Cirrhotic Patients with Tense Ascites: A Double-Blind, Placebo-Controlled, Randomized Trial," Hepato-Gastroenterology, 61:1915-1925 (2014).
Angeli et al., "Hyponatremia in Cirrhosis: Results of a Patient Population Survey," Hepatology, 44:1525-1542 (2006).
Angeli, et al., "Terlipressin Given as Continuous Intravenous Infusion Versus Terlipressin Given as Intravenous Boluses in the Treatment of Type 1 Hepatorenal Syndrome (HRS) in Patients With Cirrhosis," Journal of Hepatology, Abstract 175 of the 44th Annual Meeting of the European Association for the Study, vol. 50, Supplement 1 (2009).
Angeli, P., "Terlipressin for Hepatorenal Syndrome: Novel Strategies and Future Perspectives," Ascites, Hyponatremia and Hepatorenal Syndrome: Progress in Treatment, 28:189-197 (2011).
Angeli, "Terlipressin for the treatment of hepatorenal syndrome in patients with cirrhosis" Expert Opinion on Orphan Drugs, 1(3):241-48 (2013).
Bari et al., "The Combination of Octreotide and Midodrine Is Not Superior to Albumin in Preventing Recurrence of Ascites After Large-Volume Paracentesis," Clinical Gastroenterology and Hepatology, 10:1169-1175 (2012).
Caraceni et al., "Long-term treatment of hepatorenal syndrome as a bridge to liver transplantation," Digestive and Liver Disease, 43:242-245 (2011).
Cavallin et al., "Terlipressin Given by Continuous Intravenous Infusion Versus Intravenous Boluses in the Treatment of Hepatroenal Syndrome: A Randomized Controlled Study," Hepatology, 63(3):983-992 (2016).
Cavallin et al., "Terlipressin plus albumin versus midodrine and octreotide plus albumin in the treatment of hepatorenal syndrome: a randomized trial," Hepatology, 62(2):567-574 (2015).
Cervoni, M.D., Jean Paul et al., "Terlipressin May Influence the Outcome of Hepatorenal Syndrome Complicating Alcoholic Hepatitis," Am. J. Gastroenterol., 92(11):2113-2114 (1997).
Curriculum Vitae of Prof Paul J. Gow. Exhibit 1003 in *Mallinckrodt v. BioVie* IPR2018-00974, filed by Mallinckrodt Apr. 27, 2018, pp. 1-17,.
Declaration of Paul Gow Under 37 C.F.R. §1.68 in Support of Petition for Inter Partes Review of U.S. Pat. No. 9,655,945. Exhibit 1002 in *Mallinckrodt v. BioVie* IPR2018-00974, filed by Mallinckrodt Apr. 27, 2018, pp. 1-90.
Ding et al., "Hemodynamic effects of continuous versus bolus infusion of terlipressin for portal hypertension: A randomized comparison," Gastroenterology and Hepatology, 28:1242-1246 (2013).
Dohler, Klaus D., "Terlipressin and Hyponatremia," A short review, Curatis Pharma GmbH, (Oct. 31, 2010) (6 pages).
Fabrizi et al., "Terlipressin for hepatorenal syndrome: A meta-analysis of randomized trials," The International Journal of Artificial Organs, 32(3):133-140 (2009).
Fernández-Varo et al., "Vasopressin 1a Receptor Partial Agonism Increases Sodium Excretion and Reduces Portal Hypertension and Ascites in Cirrhotic Rats," Hepatology, 63(1):207-216 (2016).
Fimiani et al., "The use of terlipressin in cirrhotic patients with refractory ascites and normal renal function: A multicentric study," European Journal of Internal Medicine, 22:587-590 (2011).
Gadano et al., "Natriuretic response to the combination of atrial natriuretic peptide and terlipressin in patients with cirrhosis and refractory ascites," Journal of Hepatology, 26:1229-1234 (1997).
Ganne-Carrié, M.D., Nathalie et al., "Hepatorenal Syndrome Long-Term Treatment with Terlipressin as a Bridge to Liver Transplantation," Disgestive Diseases and Sciences, 41(6):1054-1056 (Jun. 1996).
Gentilini et al., "Albumin Improves the Response to Diuretics in Patients with Cirrhosis and Ascites: Results of a Randomized, Controlled Trial," Journal of Hepatology, 30:639-45 (1999).
Gerbes et al., "Terlipressin for Hepatorenal Syndrome: Continuous Infusion as an Alternative to IV Bolus Administration, with replies

(56) References Cited

OTHER PUBLICATIONS by Sanyal & Boyer and Ginès et al.," Gastroenterology, 137:1179-1181. Exhibit 2026 in *Mallinckrodt v. BioVie* IPR2018-00974, filed by BioVie on Mar. 7, 2019.
Ghosh et al., "Noradrenaline vs terlipressin in the treatment of type 2 hepatorenal syndrome: a randomized pilot study," Liver International, 33(8):1187-1193 (2013).
Gines et al., "Incidence, Predictive Factors, and Prognosis of the Hepatorenal Syndrome in Cirrhosis With Ascites," Gastroenterology, 105:229-236 (1993).
Gluud et al., "Systematic Review of Randomized Trials on Vasoconstrictor Drugs for Hepatorenal Syndrome," Hepatology, 51(2):576-584 (Feb. 2010).
Gluud et al., "Terlipressin for hepatorenal syndrome (Review)," The Cochrane Collaboration, 12(9):1-35 (2012).
Gordon, "Ascites," Clin. Liver Dis., 16:285-299 (2012).
Gow et al., "Outpatient Terlipressin Infusion for the Treatment of Refractory Ascites," The American Journal of Gastroenterology, 111:1041-1042 (Jul. 2016).
Hsu, Shao-Jung and Huang, Hui-Chun, "Management of ascites in patients with liver cirrhosis: Recent evidence and controversies," Journal of the Chinese Medical Association, 76:123-130 (2013).
Huang, Y-Y et al., "Terlipressin Resolves Ascites of Cirrhotic Rats through Downregulation of Aquaproin 2," The Journal of International Medical Research, 40:1735-1744 (2012).
Jarcuska et al., "Hemodialysis in Hepatorenal Syndrome Type 1 in Alcoholic Liver Cirrhosis Treated by Continual Terlipressin Infusion in Combination with Albumin Plasmaexpansion," Hepatology, 38(S2):194-195 (2003).
Jarcuska et al., "Hepatorenal Syndrome Type 1 in Patients with Acute Alcoholic Hepatitis Treated with Continual Terlipressin Infusion in Combination with Albumin Plasmaexpansion," Hepatology, 36(S1):256 (2002).
Kalambokis et al., "Effects of somatostatin, terlipressin and somatostatin plus terlipressin on portal and systemic hemodynamics and renal sodium excretion in patients with cirrhosis," Journal of Gastroenterology and Hepatology, 20:1075-1081 (2005).
Kalambokis et al., "Effects of terlipressin on water excretion after oral water load test in nonazotemic cirrhotic patients with ascites without hyponatremia," Scandinavian Journal of Gastroenterology, 45(12):1509-1515 (2010).
Kalambokis et al., "Vasoconstrictor Therapy for Patients with Cirrhosis with Ascites but Without Hepatorenal Syndrome," Hepatology, 48(2):686 (2008).
Krag et al., "Terlipressin Improves Renal Function in Patients with Cirrhosis and Ascites Without Hepatorenal Syndrome," Hepatology, 46:1863-1871 (2007).
Krag, Aleksander, "Efficacy and Safety of Terlipressin in Cirrhotic Patients and Variceal Bleeding or Hepatorenal Syndrome," Adv. Ther., 25(11):1105-1140 (2008).
Lange et al., "Continuous Versus Bolus Infusion of Terlipressin in Ovine Endotoxemia," Shock, 28(5) (2007) (8 pages).
Lenaerts et al., "Comparative pilot study of repeated large volume paracentesis vs the combination on clonidine-spironolactone in the treatment of cirrhosis-associated refractory ascites," Gastroenterol Clin Biol, 29(11):1137-1142 (2005).
Lim et al., "Vasoconstrictor Therapy for the Hepatorenal Therapy," Gastroenterology, 134:1608-11 (2008).
Martín-Llahí et al., "Terlipressin and Albumin vs Albumin in Patients With Cirrhosis and Hepatorenal Syndrome: a Randomized Study," Gastroenterology, 134:1352-1359 (2008).
Moreau et al., "Clinical characteristics and outcome of patients with cirrhosis and refractory ascites," Liver International, 24:457-464 (2004).
Morelli et al., "Continuous terlipressin versus vasopressin infusion in septic shock (TERLIVAP): a randomized, controlled pilot study," Critical Care, vol. 13 (2009) (14 pages).

Mulkay et al., "Long-term terlipressin administration improves renal function in cirrhotic patients with type 1 hepatorenal syndrome: a pilot study," Acta Gastro-Enterologica Belgica, 64:15-19 (Jan.-Mar. 2001).
Neri et al., "Terlipressin and Albumin in Patients with Cirrhosis and Type 1 Hepatorenal Syndrome," Dig. Dis. Sci., 53:830-835 (2008).
Nilsson et al., "Pharmacokinetics of Terlipressin After Single I.V. Doses to Healthy Volunteers," Drugs Exptl Clin. Res., 16(6):307-314 (1990).
Ortega et al., "Terlipressin Therapy With and Without Albumin for Patients With Hepatorenal Syndrome: Results of a Prospective, Nonrandomized Study," Hepatology, 36:941-948 (Oct. 2002).
Parry, "Terlipressin and Albumin Combination Therapy Improves Renal Function in HRS-1," Peer-Reviewed Highlights from AASLD: The Liver Meeting, pp. 17-18 (Dec. 2014).
Patent Owner's Preliminary Response Under 37 C.F.R. § 42.107. Paper 6 in *Mallinckrodt v. BioVie* IPR2018-00974, filed by BioVie on Aug. 15, 2018, pp. 1-45.
Petition for Inter Partes Review of U.S. Pat. No. 9,655,945 Under 35 U.S.C. §§ 311 et seq. and 37 C.F.R. § 42.100 et seq. Paper 2 in *Mallinckrodt v. BioVie* IPR2018-00974, filed by Mallinckrodt on Apr. 27, 2018, pp. 1-72.
PharmaIN Press Release, FDA Grants Orphan-Drug Designation for Novel Terlipressin Formulation for the Treatment of Ascites, PharmaIN website (Apr. 1, 2013), available at: http:/pharmain.com/fda-grants-orphan-drugdesignation-for-novel-terlipressin-formulation-for-thetreatment-of-ascites (2 pages).
Piano et al., "Continuous recurrence of type 1 hepatorenal syndrome and long-term treatment with terlipressin and albumin: A new exception to MELD score in the allocation system to liver transplantation?" Journal of Hepatology, 55:491-496 (2011).
Planas et al., "Natural History of Patients Hospitalized for Management of Cirrhotic Ascites," Clinical Gastroenterology & Hepatology, 4:1385-94 (2006).
Robertson et al., "Continuous Outpatient Terlipressin Infusion for Hepatorenal Syndrome as a Bridge to Successful Liver Transplantation," Hepatology, 60(6):2125-2126 (2014).
Rodriguez et al., "Treatment of Type 2 Hepatorenal Syndrome in Patients Awaiting Transplantation: Effects on Kidney Function and Transplantation Outcomes," Liver Transplantations, 21:1347-1354 (2015).
Runyon, M.D., Bruce A., "Management of Adult Patients with Ascites Due to Cirrhosis: Update 2012," AASLD Practice Guideline, Hepatology, pp. 1-27 (Feb. 2013).
Sagi et al., "Terlipressin therapy for reversal of type 1 hepatorenal syndrome: A meta-analysis of randomized controlled trials," Journal of Gastroenterology and Hepatology, 25(5):880-885 (2010).
Salerno et al., "Diagnosis, Prevention and Treatment of Hepatorenal Syndrome in Cirrhosis," Gut, 56(9):1310-1318 (2007).
Saner et al., "Terlipressin plus hydroxyethyl starch infusion: an effective treatment for hepatorenal syndrome," European Journal of Gastroenterology & Hepatology, 15:925-927 (2003).
Sanyal et al., "A Randomized, Prospective, Double-Blind, Placebo-Controlled Trial of Terlipressin for Type 1 Hepatorenal Syndrome," Gastroenterology, 134:1360-1368 (2008).
Singh et al., "Midodrine and Clonidine in Patients With Cirrhosis and Refractory or Recurrent Ascites: A Randomized Pilot Study," The American Journal of Gastroenterology, 108:560-567 (Apr. 2013).
Singh et al., "Midodrine in patients with cirrhosis and refractory or recurrent ascites: A randomized pilot study," Journal of Hepatology, 56:348-354 (2012).
Siqueira et al., "Refractory Ascites: Pathogeneis, Clinical Impact, and Management," Gastroenterology & Hepatology, 5(9):647-56 (Sep. 2009).
Sola et al., "Hyponatremia in Patients Treated With Terlipressin for Severe Gastrointestinal Bleeding Due to Portal Hypertension," Hepatology, 52:1783-90 (2010).
Solanki et al., "Beneficial effects of terlipressin in hepatorenal syndrome: A prospective, randomized placebo-controlled clinical trial," Journal of Gastroenterology and Hepatology, 18:152-56 (2003).

(56) References Cited

OTHER PUBLICATIONS

Tandon et al., "The effect of 1 month of therapy with midodrine, octreotide-LAR and albumin in refractory ascites: a pilot study," Liver International, 29(2):169-74 (Feb. 2009).
Therapondos et al., "Systemic, portal and renal effects of terlipressin in patients with cirrhotic ascites: Pilot Study," Journal of Gastroenterology and Hepatology, 19:73-77 (2004).
Vasudevan et al., "Efficacy of outpatient continuous terlipressin infusions for hepatorenal syndrome," Hepatology, 5 pages (2015).
Wong et al., "Effects of a selective vasopressin V2 receptor antagonist, satavaptan, on ascites recurrence after paracentesis in patients with cirrhosis," Journal of Hepatology, 53:283-90 (2010).
Wong et al., "Midodrine, Octreotide, Albumin, and TIPS in Selected Patients With Cirrhosis and Type 1 Hepatorenal Syndrome," Hepatology, 40:55-64 (2004).
Wong et al., "Working Party proposal for a revised classification system of renal dysfunction in patients with cirrhosis," Gut, 60:702-709 (2011).
Wong, "Management of ascites in cirrhosis," Journal of Gastroenterology and Hepatology, 27:11-20 (2012).
Abe & Miyasaka, Kidney and Dialysis, 70(3):361-66 (2011). (in Japanese).
English translation of Notice for Reasons for Rejection in JP Patent Application No. 2018-145654; mailed Jul. 10, 2019, pp. 1-3 (describing Abe & Miyasaka, Kidney and Dialysis, 70(3):361-66 (2011)).
The Confirm Study, "A Study to Confirm Efficacy and Safety of Terlipressin in HRS Type 1," ClinicalTrials.gov, Summary, available at clinicaltrials.gov/ct2/show/NCT02770716?term=terlipressin &recrs=abc (first posted May 12, 2016). Exhibit 2005 in *Mallinckrodt v. BioVie* IPR2018-00974, filed by BioVie on Aug. 15, 2018, pp. 1-7.
Mallinckrodt Press Release, "First Patient Enrolled in Mallinckrodt Phase 3 Terlipressin Trial," available at www.prnewswire.com/news-releases/first-patient-enrolled-inmallinckrodt-phase-3-terlipressin-trial-300305910.html (Jul. 28, 2016). Exhibit 2006 in *Mallinckrodt v. BioVie* IPR2018-00974, filed by BioVie on Aug. 15, 2018, pp. 1-5.
FDA, "What is a Serious Adverse Event?," available at web.archive.org/web/20150504051703/https://www.fda.gov/safety/medwatch/howtoreport/ucm053087.htm (last updated Jan. 10, 2014). Exhibit 2007 in *Mallinckrodt v. BioVie* IPR2018-00974, filed by BioVie on Aug. 15, 2018, pp. 1-2.
Transcript of the Deposition of Dr. Jaime Bosch, dated May 9, 2019. Exhibit 1016 in *Mallinckrodt v. BioVie* PR2018-00974, filed by Mallinckrodt on Jun. 4, 2019, pp. 1-150.
Rebuttal Declaration of Paul Gow Under 37 C.F.R. § 1.68 in Support of Petitioner's Reply. Exhibit 1017 in *Mallinckrodt v. BioVie* IPR2018-00974, filed by Mallinckrodt on Jun. 4, 2019, pp. 1-9.
Romanelli et al., "Long-term albumin infusion improves survival in patients with cirrhosis and ascites: An unblended randomized trial" World Journal of Gastroenterology, 12(9):1403-1407 (2006). Exhibit 1019 in *Mallinckrodt v. BioVie* IPR2018-00974, filed by Mallinckrodt on Jun. 4, 2019.
Testro et al., "Long-term outcome of patients treated with terlipressin for types 1 and 2 hepatorenal syndrome," Hepatology, 23:1535-1540 (2008). Exhibit 2022 in *Mallinckrodt v. BioVie* IPR2018-00974, filed by BioVie on Mar. 7, 2019.
Declaration of Dr. Jaime Bosch, MD, PhD Under 37 C.F.R. § 1.68 in Support of Patent Owner's Response. Exhibit 2023 in *Mallinckrodt v. BioVie* IPR2018-00974, filed by BioVie on Mar. 7, 2019, pp. 1-104.

Dr. Jaime Bosch's Curriculum Vitae. Exhibit 2024 in *Mallinckrodt v. BioVie* IPR2018-00974, filed by BioVie on Mar. 7, 2019, pp. 1-10.
Ginès et al., "EASL clinical practice guidelines on the management of ascites, spontaneous bacterial peritonitis, and hepatorenal syndrome in cirrhosis," Journal of Hepatology, 53:397-417 (2010). Exhibit 2027 in *Mallinckrodt v. BioVie* PR2018-00974, filed by BioVie on Mar. 7, 2019.
Testino et al., "Type-2 hepatorenal syndrome and refractory ascites: role of transjugular intrahepatic portosystemic stent-shunt in eighteen patients with advances cirrhosis awaiting orthotopic liver transplantation," Hepatogastroenterology, 50(54): 1753-5 (2003).
Moreau and Lebrec, "The use of vasoconstrictors in patients with cirrhosis: type 1 HRS and beyond," Hepatology, 43:385-394 (2006). Exhibit 2033 in *Mallinckrodt v. BioVie* IPR2018-00974, filed by BioVie on Mar. 7, 2019.
Schindler et al., "Albumin substitution improves urinary sodium excretion and diuresis in patients with liver cirrhosis and refractory ascites," Journal of Hepatology, 31:1132 (1999). Exhibit 2036 in *Mallinckrodt v. BioVie* IPR2018-00974, filed by BioVie on Mar. 7, 2019.
De Franchis et al., "Revising consensus in portal hypertension: report of the Baveno V consensus workshop on methodology of diagnosis and therapy in portal hypertension," Journal of Hepatology, 53(4):762-768 (2010). Exhibit 2037 in *Mallinckrodt v. BioVie* IPR2018-00974, filed by BioVie on Mar. 7, 2019.
De Franchis et al., "Expanding consensus in portal hypertension: Report of the Baveno VI Consensus Workshop: Stratifying risk and individualizing care for portal hypertension," Journal of Hepatology, 63(3):743-752 (2015). Exhibit 2038 in *Mallinckrodt v. BioVie* IPR2018-00974, filed by BioVie on Mar. 7, 2019.
Transcript of the Deposition of Dr. Paul Gow, dated Feb. 13, 2019. Exhibit 2039 in *Mallinckrodt v. BioVie* PR2018-00974, filed by BioVie on Mar. 7, 2019, pp. 1-154.
Supplemental Declaration of Dr. Jaime Bosch, MD, Phd Under 37 C.F.R. § 1.68 in Support of Patent Owner's Sur-Reply. Exhibit 2044 in *Mallinckrodt v. BioVie* IPR2018-00974, filed by BioVie on Jun. 28, 2019, pp. 1-13.
Patent Owner's Response Under 37 C.F.R. § 42.120. Paper 15 in *Mallinckrodt v. BioVie* IPR2018-00974, filed by BioVie on Mar. 7, 2019, pp. 1-74.
Patent Owner's Contingent Motion to Amend Under 37 C.F.R. § 42.121. Paper 16 in *Mallinckrodt v. BioVie* IPR2018-00974, filed by BioVie on Mar. 7, 2019, pp. 1-35.
Petitioner's Reply to Patent Owner's Response. Paper 18 in *Mallinckrodt v. BioVie* IPR2018-00974, filed by Mallinckrodt on Jun. 4, 2019, pp. 1-31.
Petitioner's Opposition to Patent Owner's Contingent Motion to Amend. Paper 19 in *Mallinckrodt v. BioVie* IPR2018-00974, filed by Mallinckrodt on Jun. 4, 2019, pp. 1-31.
Patent Owner's Sur-Reply to Petitioner's Reply. Paper 21 in *Mallinckrodt v. BioVie* IPR2018-00974, filed by BioVie on Jun. 28, 2019, pp. 1-37.
Patent Owner's Reply in Support of Its Contingent Motion to Amend Under 37 C.F.R. § 42.121. Paper 22 in *Mallinckrodt v. BioVie* IPR2018-00974, filed by BioVie on Jun. 28, 2019, pp. 1-23.
Patent Owner's Request for Oral Argument. Paper 23 in *Mallinckrodt v. BioVie* IPR2018-00974, filed by BioVie on Jul. 14, 2019, pp. 1-4.
Head of Medical Agencies: "Draft Public Assessment Report, Scientific discussion, Glypressin, 1mg solution for injection, Terlipressin acetate, DK/H/0829/002/MR." Sep. 23, 2010, pp. 1-6.
Gobeaux et al. "SAXS-WAXS monitoring of the amyloid fibril assembly of a hormone peptide analogue upon pH change." HAL Open Science. 2021, HAL Id:cea-03322335, 31 pages.

* cited by examiner

FORMULATIONS OF TERLIPRESSIN

CROSS REFERENCE TO RELATED APPLICATIONS

This application claims priority to U.S. Provisional Patent Application Ser. No. 62/851,366, filed May 22, 2019, the contents of which is hereby incorporated by reference in its entirety.

BACKGROUND

Field

The disclosure is directed to stable pharmaceutical compositions of terlipressin having increased concentrations at room or ambient temperature or under refrigeration.

Technical Background

Terlipressin is a synthetic vasopressin that is approved in many countries outside of the United States to treat the life-threatening complications of cirrhosis, including hepatorenal syndrome (HRS) and esophageal bleeding (EVB). Its use is limited to the hospital setting due to its short half-life (Nilsson, et al., (1990) Drugs Explt Clin. Res., XVI(6):307-314), necessitating its administration as an intravenous bolus usually every 4 to 6 hours. Additionally, terlipressin can cause side effects in up to 40% of patients. Severe side effects—including myocardial infarction, arrhythmia and intestinal infarction—can require discontinuation of treatment in up to 10% of the patients (Angeli, (2011) Ascites, Hyponatremia and Hepatorenal Syndrome: Progress in Treatment, 28:189-197). Indeed, due to the rapid vasoconstrictor properties, IV bolus dosed terlipressin must be used with caution in patients with severe asthma, severe hypertension, advanced atherosclerosis, cardiac dysrhythmias, and coronary insufficiency.

Patients with cirrhosis exhibiting type 1 hepatorenal syndrome (HRS-1) have been safely treated with terlipressin administered continuously outside the United States. Dosage ranged from 2.0-12.0 mg per 24 hours (Angeli, et al., (2009) Journal of Hepatology, 50:S73: 2.0-12.0 mg/24 h; Gerbes, (2009) Gastroenterology, 137:1179-1189: starting dose 3.0 mg/day; Robertson, et al., (2014) Hepatology, 60(6):2125-2126: 3.0 mg/day; Ding, et al., (2013), Gastroenterology and Hepatology, 28:1242-1246: 4.0 mg/day; Cavallin, et al., (2015), Hepatology, 62(2):567-574: 3-12 mg/day). In the approximately 40 countries where terlipressin is approved, it is commonly available in lyophilized powder format (Glypressin SmPC), or in certain countries as a liquid in a vial (EVERject label). These formats require preparation by a medical professional before they can be administered in the hospital setting.

Currently terlipressin is available in two formats: lyophilized powder for reconstitution or as a liquid (0.2 milligrams/mL) in vials. The lyophilized version is typically supplied in vials containing 1 mg terlipressin powder for reconstitution using the provided ampoule of 5 mL of saline solution (e.g., Glypressin, Ferring Pharmaceuticals is supplied as one vial containing 1 mg terlipressin acetate for reconstitution in 5 mL solution) to deliver 0.17 mg/mL terlipressin (0.2 mg/mL terlipressin acetate) solution for injection. Administering this product requires two or three prior steps: reconstituting the powder with diluent, withdrawing the solution, and possible further dilution, then injection by slow bolus dose directly into the patient or into the patient's intravenous line or IV bag. Glypressin requires refrigerated storage at a temperature of 2° C. to 8° C.

The liquid, terlipressin acetate 0.2 milligrams/mL solution for injection (Terlipressin acetate, Ever Pharma) is also not stable at room temperature (RT) and requires refrigerated storage at a temperature of 2° C. to 8° C. It is supplied in vials containing 5 mL or 10 mL of solution. This solution is withdrawn into a syringe for administration via bolus injection. Current formulations use acetic acid to adjust the pH of the terlipressin acetate solution.

Thus, there is a need for a pre-filled syringe product format to simplify the administration of terlipressin by administering the product directly into the patient or via intravenous line placed in the patient or IV bag. There is also a need for a formulation of terlipressin which is room temperature stable for a sustained period of time, allowing for use at home or rapid use settings such as the ICU or ambulances or in other settings where terlipressin can be administered without the need for refrigeration space and with less manipulation by the healthcare worker.

SUMMARY

One aspect of the disclosure provides an aqueous composition comprising terlipressin acetate or a pharmaceutically acceptable salt thereof, wherein the composition comprises from about 0.2 to about 10.0 mg/mL terlipressin acetate or a pharmaceutically acceptable salt thereof, wherein the pH of the composition is from about 3.4 to about 5.0.

In some embodiments of the disclosure, the composition has a sum of impurities of less than 4.5% of the total weight of the impurities and terlipressin in the composition.

In some embodiments of the disclosure, the pH of the composition is in the range of 4.0 to 5.0.

In some embodiments of the disclosure, the composition is stable at about 25° C. for at least 24 months and at 30° C. and about 75% relative humidity for at least six months, or at about 30° C. to about 40° C. and about 75% relative humidity for up to 26 weeks, or at about 25° C. and about 60% relative humidity for up to 2 years.

In some embodiments of the disclosure, the composition is stored at 2° C. to 8° C.

In some embodiments of the disclosure, the composition comprises a stabilizing agent. In some embodiments of the disclosure, the stabilizing agent is aspartic acid.

In some embodiments of the disclosure, the composition comprises an isotonicity agent. In some embodiments of the disclosure, the isotonicity agent is dextrose or sodium chloride.

In some embodiments of the disclosure, the composition comprises a pH adjusting agent. In some embodiments of the disclosure, the pH adjusting agent is hydrochloric acid, potassium hydroxide, acetic acid, sodium hydroxide, or potassium hydroxide.

Another aspect of the disclosure provides a pre-filled syringe comprising an aqueous composition comprising terlipressin acetate or a pharmaceutically acceptable salt thereof, wherein the composition comprises from about 0.2 to about 10.0 mg/mL terlipressin acetate or a pharmaceutically acceptable salt thereof, wherein the pH of the composition is from about 3.4 to about 5.0.

In some embodiments of the disclosure, a head space within the syringe comprises nitrogen.

Yet another aspect of the disclosure provides a kit comprising an aqueous composition comprising terlipressin acetate or a pharmaceutically acceptable salt thereof, wherein the composition comprises from about 0.2 to about 10.0 mg/mL terlipressin acetate or a pharmaceutically acceptable salt thereof, wherein the pH of the composition is from about 3.4 to about 5.0, wherein the kit comprises a container for the composition, wherein the container optionally has a means for injecting the composition into a subject.

In some embodiments of the disclosure, the container is a syringe that is pre-filled with the composition. In other embodiments of the disclosure, the pre-filled syringe is made of glass or plastic.

In some embodiments of the disclosure, the kit further comprises a needle and/or a syringe rod.

In some embodiments of the disclosure, the kit further comprises instructions for administering the composition. In other embodiments of the disclosure, the instructions provide administering the composition by continuous infusion or as a bolus intravenous dose.

In some embodiments of the disclosure, the continuous infusion is administered with an ambulatory pump or other controlled delivery device.

In some embodiments of the disclosure, the instructions provide the option of administering the composition by injecting the composition into a container of diluent that can then be connected to or inserted into an ambulatory pump for continuous infusion.

Yet another aspect of the disclose provides an aqueous composition, consisting of: terlipressin or a pharmaceutically acceptable salt thereof, a pharmaceutically acceptable solvent, a stabilizing agent, an isotonicity agent, and a pH adjusting agent, wherein the composition comprises from 0.2 mg/mL to 10.0 mg/mL terlipressin or a pharmaceutically acceptable salt thereof, wherein the composition has a pH from about 3.4 to about 5.0, wherein after the composition is stored at about 40° C. and about 75% relative humidity for 12 weeks, and wherein the composition has a sum of impurities of less than about 4.5% of the total weight of the impurities and terlipressin in the composition.

In some embodiments of the disclosure, the composition consists of: terlipressin or a pharmaceutically acceptable salt thereof in the amount of about 0.5 mg/mL to about 10.0 mg/mL, aspartic acid in the amount of about 0.1 mg/mL to about 2 mg/mL, dextrose, succinic acid, sodium hydroxide, and water.

In other embodiments of the disclosure, the composition consists of: terlipressin or a pharmaceutically acceptable salt thereof in the amount of from about 0.2 mg/mL to about 1.0 mg/mL, sodium acetate, sodium hydroxide, and water.

In yet other embodiments of the disclosure, the composition consists of: terlipressin or a pharmaceutically acceptable salt thereof in the amount of 0.2 mg/mL, methionine in the amount of about 1.0 mg/mL, dextrose in the amount of about 50.0 mg/mL, succinic acid in the amount of about 1.2 mg/mL, sodium hydroxide, and water.

In some embodiments of the disclosure, the pharmaceutically acceptable solvent is water.

In some embodiments of the disclosure, the stabilizing agent is aspartic acid, acetic acid, adipic acid, citric acid, maleic acid, succinic acid, or phosphate.

In some embodiments of the disclosure the isotonicity agent is dextrose or sodium chloride.

In some embodiments of the disclosure the pH adjusting agent is acetic acid, hydrochloric acid or sodium hydroxide.

DESCRIPTION OF THE FIGURES

The foregoing aspects and other features of the disclosure are explained in the following description, taken in connection with the accompanying drawings, wherein.

DESCRIPTION

Figure 1:
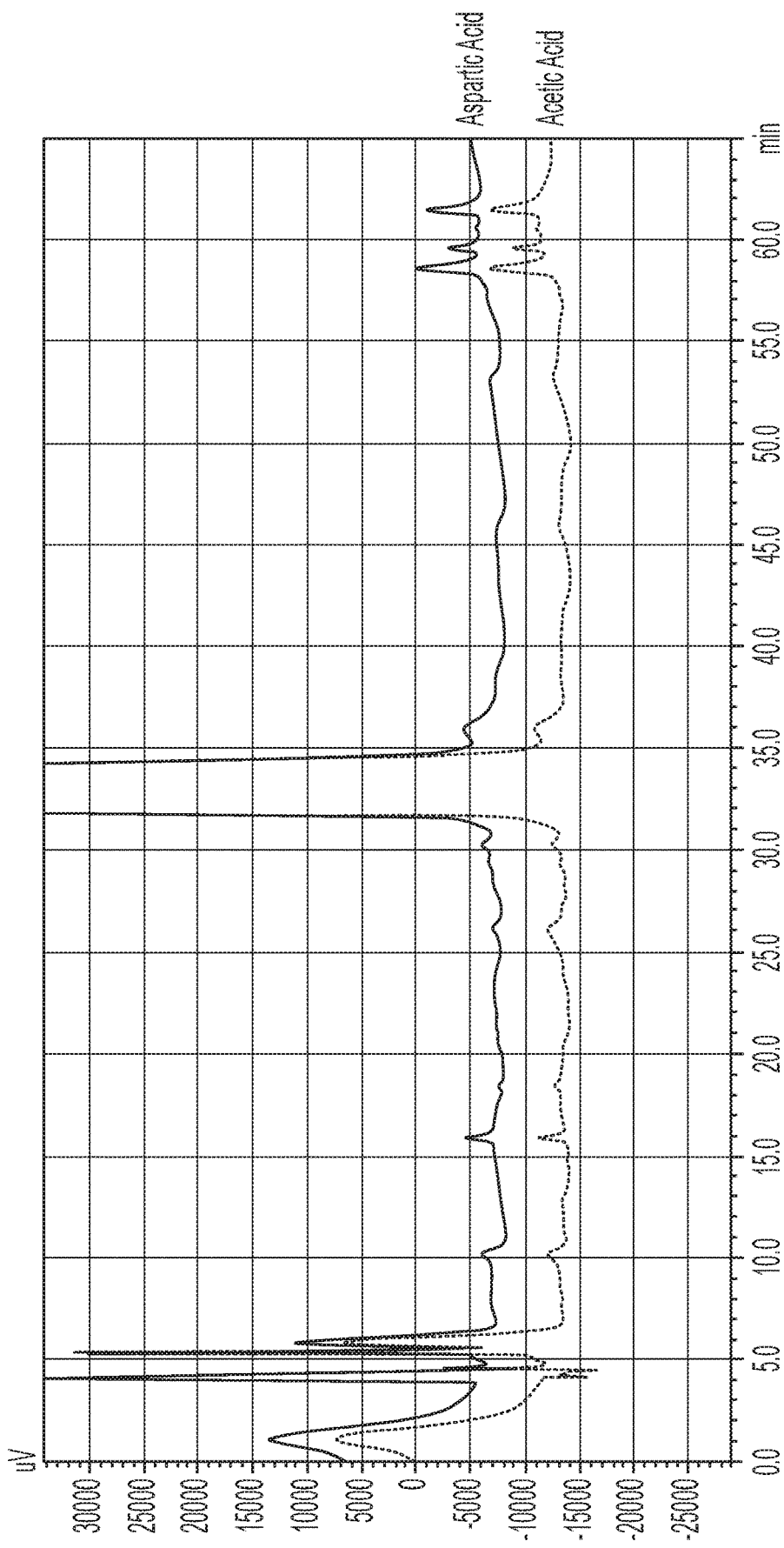
FIG. 1 is overlapping HPLC chromatograms for acetic acid and aspartic acid terlipressin formulations (without nitrogen protection) at pH 4.5 for three months at 2° C.-8° C.

The disclosure is directed to liquid formulations of terlipressin that have been optimized for a pre-filled syringe product format and that simplify drug delivery, particularly for the rapid use and outpatient settings. In one aspect, the formulation can be injected into a diluent container that is connected to or inserted into an ambulatory pump to controllably infuse the diluent/terlipressin into the patient. Alternatively, the formulations can be infused directly without dilution or administered as an IV bolus.

Definitions

Articles "a" and "an" are used herein to refer to one or to more than one (i.e., at least one) of the grammatical object of the article. By way of example, "an element" means at least one element and can include more than one element.

As used herein, the term "and/or" includes any and all combinations of one or more of the associated listed items. It will be further understood that the use herein of the terms "including," "comprising," or "having," and variations thereof, is meant to encompass the elements listed thereafter and equivalents thereof as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, are expressly enumerated in this specification. These are only examples of what is specifically intended, and all possible combinations of numerical values between and including the lowest value and the highest value enumerated are to be considered to be expressly stated in this disclosure.

The term "about" in association with a numerical value means that the numerical value can vary plus or minus by 5% or less of the numerical value.

The term "excipient" includes a non-therapeutic agent added to a pharmaceutical composition to provide a desired consistency or stabilizing effect. Suitable pharmaceutical excipients include, but are not limited to, starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The term "patient" refers to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. The patient can be a human patient that is at risk for, or suffering from, a complication of cirrhosis (e.g., ascites).

The term "pharmaceutical composition" or "pharmaceutical formulation" refers to preparations which are in such form as to permit the biological activity of the active ingredient to be unequivocally effective, and which contain no additional components which are significantly toxic to the subjects to which the formulation would be administered. "Pharmaceutically acceptable" excipients (vehicles, additives) are those which can reasonably be administered to a patient to provide an effective dose of the active ingredient employed.

The term "pharmaceutically acceptable carrier" is recognized in the art and includes a pharmaceutically acceptable material, composition or vehicle, suitable for administration to mammals. The carriers include liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient.

Terlipressin (also referred to herein as terlipressin acetate) is a synthetic triglycyllysine derivative of vasopressin with vasoconstrictive, antihemorrhagic, and antidiuretic properties. Terlipressin is an inactive peptide prodrug having an amino acid sequence of GGGCYFQNCPKG that is biotransformed upon administration to its more active form, lysine vasopressin. Suitable salts of terlipressin include, but are not limited to, terlipressin acetate.

Stable Aqueous Formulations of Terlipressin

Aqueous pharmaceutical compositions of the disclosure comprising terlipressin acetate or pharmaceutically active salt thereof, and having pH within about 3.4 to about 5.0 can be stored at room temperature (e.g., at about 25° C. and about 60% relative humidity) for a sustained period (e.g., up to about 2 years). The aqueous compositions comprising terlipressin acetate or other pharmaceutically active salt thereof of the disclosure exhibit improved stability at higher concentrations (e.g., at or above about 0.2 mg/mL) because the formulations can prevent peptides aggregation and loss of stability that is typical for peptides when stored in a concentrated liquid form.

A "stable" composition is one in which the active ingredient therein (e.g., terlipressin) essentially retains its physical stability and/or chemical stability and/or biological activity upon storage.

A composition "retains its physical stability" in a pharmaceutical formulation if it shows substantially no signs of aggregation, and/or precipitation upon visual examination of color and/or clarity, or as measured by UV light scattering or by size exclusion chromatography. A composition "retains its chemical stability" in a pharmaceutical formulation, if the chemical stability at a given time is such that the active ingredient (e.g., terlipressin) undergoes minimal alterations when analyzed by stability indicated chromatographic method.

One aspect of the disclosure provides an aqueous composition comprising terlipressin acetate or a pharmaceutically acceptable salt thereof, wherein the composition comprises from about 0.2 to about 10.0 mg/mL terlipressin acetate or a pharmaceutically acceptable salt thereof, wherein the pH of the composition is from about 3.4 to about 5.0.

As used herein, the term "aqueous" refers to a solution in which the solvent is water. The solvent can be sterile water suitable for injection. In one embodiment, the solvent can be bacteriostatic water. In other embodiments, the solvent can be mixtures of water with other pharmaceutically acceptable solvents or pharmaceutically acceptable alcohols or other bacteriostatic agents (e.g., benzyl alcohol).

The concentration of terlipressin in the liquid (e.g. aqueous composition) can be, for example, 0.2 mg/mL, 0.5 mg/mL, 1.0 mg/mL, 2.0 mg/mL, 5.0 mg/mL, or 10.0 mg/mL, etc. In some embodiments, the composition comprises from about 0.2 mg/mL to about 10.0 mg/mL, about 0.5 mg/mL to about 10.0 mg/mL, about 1.0 mg/mL to about 9.0 mg/ml, about 1.5 mg/mL to about 8.5 mg/mL, from about 2.0 mg/mL to about 8.0 mg/mL, about 2.5 mg/mL to about 7.5 mg/mL, about 3.0 mg/mL to about 7.0 mg/mL, about 3.5 mg/mL to about 6.5 mg/mL, about 0.5 mg/mL to about 2.0 mg/mL, or about 0.5 mg/mL to about 1.0 mg/mL, mg/mL terlipressin acetate or a pharmaceutically acceptable salt thereof.

In some embodiment, the pH of the composition can be from about 3.4 to about 5.0, from about 3.5 to about 5.0, from about 3.6 to about 5.0, from about 3.7 from about 5.0, from about 3.8 to about 5.0, from about 3.9 to about 5.0, from about 4.0 to about 5.0, from about 4.1 to about 5.0, from about 4.2 to about 5.0, from about 4.3 to about 5.0, from about 4.4 to about 5.0, from about 4.5 to about 5.0, from about 4.6 to about 5.0, from about 4.7 to about 5.0, from about 4.8 to about 5.0, or from about 4.9 to about 5.0. In other embodiments, the pH of the composition can be about 3.4, 3.5, 3.6, 3.7, 3.8, 3.9, 4.0, 4.1, 4.2, 4.3, 4.4, 4.5, 4.6, 4.7, 4.8, 4.9, 5.0, or 5.1.

An advantage of the compositions of the disclosure is their improved stability at room temperature (or ambient temperature). As used herein, the term room temperature stability or stable at room temperature means that the composition is capable of being stored at room temperature without degrading or losing efficacy as compared to a similar composition that is stored under refrigerated conditions (e.g., at about 2° C. to about 8° C.). Examples of room temperature stability include compositions that are stable at about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., or 45° C. for a sustained amount of time and at a relative humidity of about 55%, 56%, 57%, 58%, 59%, 60%, 61%, 62%, 63%, 64%, 65%, 66%, 67%, 68%, 69%, 70%, 71%, 72%, 73%, 74%, 75%, 76%, 78%, 79%, or 80%.

Relative humidity refers to the ratio of partial pressure of water vapor to the equilibrium vapor pressure of water at a given temperature. Relative humidity depends on the temperature and pressure of the environment of interest (e.g., a patient's home or other outpatient setting, or ambulance). Relative humidity can be expressed as a percentage, with a higher percentage meaning that the air-water mixture is more humid. For example, 100% relative humidity means that the air is saturated and is at its dew point.

A sustained amount of time can be for at least three weeks, at least 1 month, at least 2 months, at least 3 months, at least 4 months, at least 5 months, at least 6 months, at least 7 months, at least 8 months, at least 9 months, at least 10 months, at least 12 months, at least 15 months, at least 18 months, at least 21 months, at least 24 months, at least 28 months, at least 32 months, at least 36 months, at least 40 months, at least 5 weeks, at least 6 weeks, at least 7 weeks, at least 9 weeks, at least 10 weeks, at least 11 weeks, at least 13 weeks, at least 14 weeks, at least 15 weeks, at least 17 weeks, at least 18 weeks, at least 19 weeks, at least 21 weeks, at least 22 weeks, at least 23 weeks, at least 25 weeks, at least 26 weeks, at least 27 weeks, at least 29 weeks, at least 30 weeks, at least 1 year, at least 2 years, at least 3 years, or at least 4 years.

The compositions of the disclosure can be stable at any combination of any of the described temperatures, relative humidity percentages, and timeframes. For example, in some embodiments, the composition is stable at about 25° C. for at least 24 months, or at about 30° C. and about 75% relative humidity for at least six months. In other embodiments, the composition is stable at about 30° C. to about 40° C. and about 75% relative humidity for up to 26 weeks. In yet other embodiments, the composition is stable at about 25° C. and about 60% relative humidity for up to 2 years. In yet other embodiments, the composition is stable at about 40° C. and about 75% relative humidity for about 12 weeks.

In some embodiments of the disclosure, the composition does not need to be stored under refrigerated conditions and is stable at room temperature for a sustained amount of time. In other embodiments, the composition is stored under refrigerated conditions of about 2° C. to about 8° C., about 1° C. to about 4° C., or at about 4° C. The composition can be stored under refrigerated conditions before administering to a patient or before being stored at room temperature for a sustained amount of time and before administering to a patient.

The compositions described herein demonstrate prolonged stability against the formation of impurities. Impurities can be hydrolytic products, degradation products, and/or enantiomers of terlipressin. Examples of impurities include, but are not limited to, [6-D-phenylalanine]terlipressin, des-(1-3)-terlipressin, des-1,2-glycine-terlipressin, des-1-glycine-terlipressin, [8-L-β-aspartic acid] terlipressin, [8-L-α-aspartic acid] terlipressin, [12-glycine]terlipressin & [7-L-glutamic acid] terlipressin, [8-L-aspartic acid, 12 glycine] terlipressin], N' Acetylterlipressin, [7-L-glutamic acid, 12-glycine] terlipressin, and/or [12-glycine] terlipressin ethyl ester, or combinations thereof. Impurities in a composition can be identified by HPLC analysis.

In some embodiments, the composition has a sum of impurities of less than about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9% or about 5.0% of the total weight of the impurities and terlipressin in the composition. In other embodiments, the composition has a sum of impurities of less than about 5.0% of the total weight of the impurities and terlipressin in the composition. Non-limiting examples of the sum of impurities include 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8% of the total weight of the impurities and terlipressin in the composition.

The sum of impurities can be determined by analyzing the composition using chromatography under conditions described in the below examples. Formulation studies can be conducted to reduce the level of impurities formed during the shelf-life of the composition.

In some embodiments, the stability of the composition can have reduced formation of impurities as compared to the commercial formulation of Glypressin and can reflect a reduced formation of impurities as compared to levels of Glypressin stored under the same conditions.

The composition can include a stabilizing agent (or buffering agent), for example a pharmaceutically acceptable stabilizing agent. As used herein, the term "stabilizing agent" refers to an agent that is capable of driving an acidic or basic solution to a certain pH state, and then preventing a change from that state; in other words a stabilizing agent is an agent which is added to an already acidic or basic solution to modify the pH and then maintain the pH at the modified level.

A stabilizing agent can be a weak acid or a weak base that would be comprised in a buffer solution, and be responsible for the buffering action seen in these solutions. The stabilizing agent can be, for example, acetic acid, adipic acid, aspartic acid, citric acid, maleic acid, succinic acid or phosphate (e.g., sodium phosphate or sodium phosphate dibasic dihydrate). In some embodiments, the stabilizing agent is aspartic acid. The composition can comprise a single stabilizing agent (i.e., does not include two or more stabilizing agents). The composition can also comprise two or more stabilizing agents (e.g., citric acid and sodium phosphate).

The composition can also comprise a stabilizing solution (or buffer solution). As used herein, term stabilizing solution means a solution including a mixture of a weak acid and its conjugate base or a weak base and its conjugate acid, which has the property that the pH of the solution changes very little when a small amount of strong acid or base is added, such that the pH of the buffer or buffer solution is maintained. The stabilizing solution can be, for example, a citrate stabilizing solution, comprising citric acid and a citrate (e.g., sodium citrate), a succinate stabilizing solution comprising succinic acid and a succinate (e.g., sodium succinate), an aspartate stabilizing solution comprising aspartic acid and aspartate (e.g., monosodium aspartate), an acetate stabilizing solution comprising acetic acid and an acetate (e.g., sodium acetate), a citrate/phosphate stabilizing solution comprising citric acid and phosphate, or a phosphate stabilizing solution comprising phosphate (e.g. monosodium phosphate) and its conjugate base, (e.g., disodium phosphate). In some embodiments, the stabilizing solution is an aspartate stabilizing solution. The composition can include a single stabilizing solution (i.e., does not include two or more stabilizing solution). The composition can also include two or more stabilizing solutions (e.g., a succinate stabilizing solution and an acetate stabilizing solution).

The inventors have found that inclusion of an aspartic acid stabilizing agent (or use of an aspartate stabilizing solution) can provide effective room temperature stability. Use of an aspartic acid stabilizing agent (or an aspartate stabilizing solution) can also confer additional advantages over other stabilizing agents, including, for example, reducing injection site reactions and associated pain that occurs following administering terlipressin formulations. In some embodiments, the aspartic acid stabilizing agent can be used at a concentration of about 0.05 mg/ml to about 10 mg/ml, for example, 0.1 mg/ml to about 10 mg/ml, 0.05 mg/ml to about 9 mg/ml, 1 mg/ml to about 8 mg/ml, 0.5 mg/ml to about 6 mg/ml. Examples of particular concentrations include 0.05 mg/ml, 0.1 mg/ml, 0.5 mg/ml, 1 mg/ml, 2 mg/ml, 3 mg/ml, 4 mg/ml, 5 mg/ml, 6 mg/ml, 7 mg/ml, 8 mg/ml, 9 mg/ml or 10 mg/ml. Similarly, an acetic acid stabilizing agent can be used and in some embodiments at a concentration of about 0.02 mg/ml to about 4.2 mg/ml for acetic acid, for example, about 0.02 mg/ml to about 4 mg/ml, about 0.02 mg/ml to about 3 mg/ml about 0.03 mg/ml to about 2 mg/ml, or about 0.5 to about 1 mg/ml. For example, the acetic acid stabilizing agent can be used at a concentration of about 0.02 mg/ml, 0.03 mg/ml, 0.05 mg/ml, 0.1 mg/ml, 0.5 mg/ml, 1 mg/ml, 2 mg/ml, 3 mg/ml, 4 mg/ml, or 4.2 mg/ml.

The composition can further comprise a pH-adjusting agent. A pH adjusting agent can include, but is not limited to, acetic acid, hydrochloric acid or sodium hydroxide.

The composition can include an anti-oxidant agent. The anti-oxidant agent can be any anti-oxidant commonly used in the art, for example any anti-oxidant approved for use as a pharmaceutical excipient. For example, the anti-oxidant can be methionine, EDTA, butylated hydroxy toluene, sodium metabisulfite, ascorbic acid, or L-cysteine. The anti-oxidant can be in an amount of 0.01% to 10% (w/v), for example 0.05% to 5% (w/v) or 0.08% to 1% (w/v). The anti-oxidant can be methionine, EDTA, or a combination of methionine and EDTA. For example, the antioxidant is methionine and is in an amount of 0.5% w/v. In another example, the antioxidant is EDTA and is in an amount of 0.1% w/v.

In some embodiments, the composition does not include an anti-oxidant agent. Oxygen can be excluded during manufacturing and the container or closure system contains only low levels of oxygen, thus eliminating the need for an anti-oxidant agent in the composition. Liquid formulations can be stored in an oxygen-deprived environment. Oxygen-deprived environments can be generated by storing the formulations under an inert gas such as, for example, nitrogen or argon. In some embodiments, the head space within the container for the composition includes nitrogen for protection of the composition from oxygen.

The composition can further comprise an isotonicity agent. "Isotonic" is a term recognized in the art. Isotonic can mean, for example, that the composition of interest has essentially the same osmotic pressure as human blood. Isotonic composition will generally have an osmotic pressure from about 250 to 350 mOsm. Isotonicity can be measured using a vapor pressure or ice-freezing type osmometer, for example. An "isotonicity agent" is a compound which renders the composition isotonic.

Isotonicity agents such as mannitol or sodium chloride (NaCl) are well known in the art. The isotonicity agent can be in an amount sufficient to provide an isotonic composition (solution), for example in an amount of 0.01% to 10% (w/v). The isotonicity agent can be dextrose. If the isotonicity agent is dextrose it can be in an amount of 0.5% to 7.5% (w/v), or 4.0% to 5.5% (w/v), for example 5.0% (w/v). If the isotonicity agent is mannitol it can be in an amount of 0.05% to 7.5% (w/v). If the isotonicity agent is NaCl it can be in an amount of 0.05% to 1.2% (w/v), more preferably 0.08% to 1% (w/v), for example 0.9% (w/v). The isotonicity agent can be in an amount of about 0.1 mg/mL to about 100.0 mg/mL, for example about 0.5 mg/mL to 7.0 mg/mL or about 1.0 mg/mL to about 5.0 mg/mL. For example, if the isotonicity agent is dextrose it may be in an amount of 5.0 mg/mL to 75.0 mg/mL, for example 40.0 mg/mL to 55 mg/mL. If the isotonicity agent is NaCl it can be in an amount of 0.5 mg/mL to 12 mg/mL, for example 8.0 mg/mL to 10.0 mg/mL.

In some embodiments, the aqueous composition consists of terlipressin or a pharmaceutically acceptable salt thereof, a pharmaceutically acceptable solvent, a stabilizing agent, an isotonicity agent, and a pH adjusting agent, wherein the composition comprises from 0.2 mg/mL to 10.0 mg/mL terlipressin or a pharmaceutically acceptable salt thereof, wherein the composition has a pH from about 3.4 to about 5.0, wherein after the composition is stored at about 40° C. and about 75% relative humidity for 12 weeks, and wherein the composition has a sum of impurities of less than about 4.5% of the total weight of the impurities and terlipressin in the composition. In other embodiments, the composition is storage stable reflecting the ability to remain within label specifications for at least 6 months, at least 12 months, at least 18 months, or at least 24 months when stored at room temperature. The stabilizing agent may be aspartic acid in an amount of about 0.05-10 mg/ml for aspartic acid or acetic acid in an amount of about 0.02 mg/ml-4.2 mg/ml.

In some embodiments, the composition does not contain a quaternary ammonium or disinfectant compound (e.g., benzalkonium chloride, didecyldimonium chloride).

In some embodiments, the composition contains bacteriostatic/fungistatic agents as anti-microbial preservatives (e.g. including but not limited to parabens, chlorbutanol, benzyl alcohol, phenol, thimerosal).

In some embodiments, the composition consists of: terlipressin or a pharmaceutically acceptable salt thereof in the amount of about 0.2 mg/mL to about 10.0 mg/mL, aspartic acid in the amount of about 0.1 mg/mL to about 2 mg/mL, dextrose, succinic acid, sodium hydroxide, and water. In other embodiments, the composition consists of: terlipressin or a pharmaceutically acceptable salt thereof in the amount of from about 0.2 mg/mL to about 10 mg/mL, sodium acetate, sodium hydroxide, and water. In yet other embodiments, the composition consists of: terlipressin or a pharmaceutically acceptable salt thereof in the amount of 0.2 to 10 mg/mL, methionine in the amount of about 1.0 mg/mL, dextrose in the amount of about 50.0 mg/mL, succinic acid in the amount of about 1.2 mg/mL, sodium hydroxide, and water.

In some embodiments, the disclosure is directed to an aqueous formulation consisting essentially of terlipressin acetate or a pharmaceutically acceptable salt thereof and a stabilizing agent at concentrations to enable stability during long-term storage at room temperature. In this aspect, the terlipressin concentration is about from about 0.2 to about 10.0 mg/mL and the stabilizing agent is from about 0.05-10 mg/ml aspartic acid or about 0.02 mg/ml-4.2 mg/ml acetic acid. In addition, the composition may include an isotonicity agent and optionally a pH-adjusting agent. The formulation has a sum of impurities of less than 4.5% of the total weight of the impurities and terlipressin in the composition. The pH of the composition is from about 3.4 to about 5.0.

In the various aspects of the disclosure, a terlipressin formulation is storage stable for several months or more at room temperature or accelerated storage conditions when the amount of terlipressin in the formulation is at least 90% of the terlipressin in the formulation at the time of initial manufacturing or packaging (label strength ("LS"). For example, a stable formulation of the disclosure has a LS of at least 90% after 6 months of storage at room temperature or accelerated conditions. More particularly, a stable terlipressin formulation of the disclosure has an LS of at least 91%, 92%, 93%, 94%, 95%, 96%, 97%, 98%, or 99% after at least 6, at least 12, at least 18, or at least 24 months of storage at room temperature or accelerated storage conditions. In addition, the amount of impurities present in the formulation may be less than 1%, less than 2%, less than 3%, less than 4%, less than 5%, less than 6%, less than %, less than 8% or less than 9% after the storage of the formulation.

The composition can be for any route of drug administration, e.g. oral, buccal, nasal, transdermal (e.g. patch technology), parenteral, intravenous, intramuscular or subcutaneous injection, intracisternal, intraperitoneal. In some embodiments, the composition is for intravenous administration, e.g. by continuous infusion or by a bolus IV dose. As indicated above, compositions suitable for intravenous administration can remain stable in solution at room temperature for a sustained period of time.

The compositions of the disclosure can be for use in (or in the manufacture of medicaments for) treating or preventing complications of cirrhosis in a patient in need thereof. Complications of cirrhosis can include ascites, HRS, jaundice, hepatic encephalopathy, and esophageal or gastric variceal hemorrhage. For example, the compositions can be for use in the treatment or prevention of ascites due to cirrhosis.

Another aspect of the disclosure provides a kit comprising the compositions of the disclosure, wherein the kit comprises a container for the composition, wherein the container optionally has a means for injecting the composition into a subject.

The container can be, for example, a syringe, a vial, a bottle, an ampule, or a cartridge. The container can be made from any material that is suitable for sustained storage at room temperature, including, but not limited to, glass, plastic, or metal. The container can be sterile before it is filled with the aqueous composition. The container can also block natural and/or artificial UV light such that the composition is protected from photodegradation or other chemical reactions that can affect the stability of the composition (e.g., the container is made from amber glass or plastic, or contains a foil packet as outer wrapping).

In some embodiments the container (e.g., a pre-filled syringe) can contain a volume of the aqueous composition of 1 mL to 10 mL, for example, 10 mL, 5 mL, 3.5 mL, 3.0 mL, 2.5 mL, 2.0 mL, 1.5 mL, or 1.0 mL.

In some embodiments, the container (e.g, pre-filled syringe) can comprise a fluoropolymer film coating and a stopper having a closure (e.g., cap, stopper) that may have a fluoropolymer-coated coating on any product-contact surface.

In some embodiments, the kit further comprises a needle and/or a syringe rod that can be attached to the container.

The kit can further comprise instructions for administering the composition. In some embodiments, the instruction provide for administering the composition by continuous infusion or as a bolus intravenous dose. Administering the composition by continuous infusion can be achieved, for example, by using an ambulatory infusion pump, programmable syringe pump, a mini infusion pump, a micro infusion pump, a fusion touch pump, an osmotic pump, a syringe touch pump, a syringe pump, or other controlled delivery device.

In some embodiments, the kit instructions provide the option of administering the composition by injecting the composition into a bag of diluent (e.g., saline or dextrose) that can then be connected to or inserted into an infusion pump for continuous infusion.

Stability of the compositions can be determined in a number of ways at specified time points, including determination of pH, visual inspection of color and appearance, determination of total peptide content by methods known in the art, e.g., UV spectroscopy, and purity is determined by, for example, SDS-PAGE, size-exclusion and UV HPLC.

The following examples are offered by way of illustration and not by way of limitation.

EXAMPLES

Analytical Methods

The analytical methods described herein are specified in the European Pharmacopeia for analysis of terlipressin acetate API. It consists of a gradient system with two mobile phases. The following parameters were used for the analyses of terlipressin acetate solutions: Column: X-Terra MS C18 4.6×250 mm 3.5 μm; Wavelength: 210 nm; Flow Rate: 0.6 mL/min; Column Oven: 30° C.; Autosampler temp: 5° C.; Injection Volume: 50 μL; Run Time: 75 min; Mobile phase: Gradient; Buffer: 3.30 g ammonium sulfate in 5 L water for chromatography; 1.0 mL sulfuric acid; Eluent A:Methanol: Buffer (18.5:81.5 v/v); Eluent B:Methanol:Buffer (35:65 v/v). The gradient conditions are shown in Table 1.

TABLE 1

Gradient Conditions

| Gradient: Time (min) | % Eluent A | % Eluent B |
|---|---|---|
| 0 | 80 | 20 |
| 45 | 80 | 20 |
| 55 | 0 | 100 |
| 65 | 0 | 100 |
| 65.01 | 80 | 20 |
| 75 | 80 | 20 |

Example 1: Aspartic Acid Formulations

Terlipressin acetate formulations containing aspartic acid (with and without nitrogen) at a pH of 4.5 are prepared.

With Nitrogen Protection: Perform all procedures using N2 protection. Sparge water for injection (WFI) prior to addition of materials. Overlay N2 during mix operations, discontinuing only to add solid materials. Keep solution at 20-25° C.

Add WFI to formulation vessel, equivalent to 80% of the final QS volume.

Add aspartic acid to WFI; rinse aspartic acid weighing vessel with WFI (rinse volume</=to 3% of final volume). Mix to dissolve Adjust pH to 4.0 with 0.1 N NaOH solution.

Add terlipressin acetate with WFI rinses (rinse volume</=5% of QS volume). Mix to dissolve.

Adjust pH to 4.5 with either 0.1 N NaOH or 0.1 N acetic acid solution (expect the pH to be 4.6 after addition of terlipressin acetate to pH 4.0 solution).

Bring to final volume with low 02 WFI. Readjust pH if required.

Without Nitrogen Protection: Keep solution at 20-25° C.

Add WFI to formulation vessel, equivalent to 80% of the final QS volume.

Add aspartic acid to WFI; rinse aspartic acid weighing vessel with WFI (rinse volume</=to 3% of final volume). Mix to dissolve.

Adjust pH to 4.0 with 0.1 N NaOH solution.

Add terlipressin acetate with WFI rinses (rinse volume</=5% of QS volume). Mix to dissolve.

Adjust pH to 4.5 with either 0.1 N NaOH or 0.1 N acetic acid solution (expect the pH to be 4.6 after addition of terlipressin acetate to pH 4.0 solution).

Bring to final volume with WFI. Readjust pH if required.

The terlipressin aspartic acid formulations are shown in Tables 2 and 3.

TABLE 2

Aspartic Acid Formulation at pH 4.5

| Component | Amount per mL | Function |
|---|---|---|
| Terlipressin acetate | 1.0 mg/mL | Active ingredient |
| Aspartic acid | 0.46 mg/mL | Stabilizing agent |
| 0.1N NaOH | To adj. pH | pH adjustment |
| 0.1N Acetic Acid | To adj. pH | pH adjustment |
| Water for Injection | QS | solvent |

TABLE 3

Aspartic Acid Formulation with Nitrogen at pH 4.5

| Component | Amount per mL | Function |
|---|---|---|
| Terlipressin acetate | 1.0 mg/mL | Active ingredient |
| Aspartic acid | 0.46 mg/mL | Stabilizing agent |
| 0.1N NaOH | To adj. pH | pH adjustment |
| 0.1N Acetic Acid | To adj. pH | pH adjustment |
| Nitrogen | N/A | Protection from oxygen |
| Water for Injection | QS | solvent |

Example 2: Acetic Acid Formulations

Terlipressin acetate formulations containing acetic acid (with and without nitrogen) at a pH of 4.5 are prepared.

With Nitrogen Protection: Perform all procedures using N2 protection. Sparge WFI prior to addition of materials. Overlay N2 during mix operations, discontinuing only to add solid materials. Keep solution at 20-25° C.

Add WFI to formulation vessel, equivalent to 80% of the final QS volume.

Add acetic acid to WFI; rinse ascetic acid weighing vessel with WFI (rinse volume</=to 3% of final volume). Mix to dissolve Adjust pH to 4.0 with 0.1 N NaOH solution.

Add terlipressin acetate with WFI rinses (rinse volume</=5% of QS volume). Mix to dissolve.

Adjust pH to 4.5 with either 0.1 N NaOH or 0.1 N acetic acid solution (expect the pH to be 4.6 after addition of terlipressin acetate to pH 4.0 solution).

Bring to final volume with low O2 WFI. Readjust pH if required.

Without Nitrogen Protection: Keep solution at 20-25° C.

Add WFI to formulation vessel, equivalent to 80% of the final QS volume.

Add ascetic acid to WFI; rinse aspartic acid weighing vessel with WFI (rinse volume</=to 3% of final volume). Mix to dissolve Adjust pH to 4.0 with 0.1 N NaOH solution.

Add terlipressin acetate with WFI rinses (rinse volume</=5% of QS volume). Mix to dissolve.

Adjust pH to 4.5 with either 0.1 N NaOH or 0.1 N acetic acid solution (expect the pH to be 4.6 after addition of terlipressin acetate to pH 4.0 solution).

Bring to final volume with WFI. Readjust pH if required.

The terlipressin acetic acid formulations are shown in Tables 4 and 5.

TABLE 4

Acetic Acid Formulation at pH 4.5

| Component | Amount per mL | Function |
|---|---|---|
| Terlipressin acetate | 1.0 mg/mL | Active ingredient |
| Acetic acid | 0.21 mg/mL | Stabilizing agent |
| 0.1N NaOH | To adj. pH | pH adjustment |
| 0.1N Acetic Acid | To adj. pH | pH adjustment |
| Water for Injection | QS | solvent |

TABLE 5

Acetic Acid Formulation with Nitrogen at pH 4.5

| Component | Amount per mL | Function |
|---|---|---|
| Terlipressin acetate | 1.0 mg/mL | Active ingredient |
| Acetic acid | 0.21 mg/mL | Stabilizing agent |
| 0.1N NaOH | To adj. pH | pH adjustment |
| 0.1N Acetic Acid | To adj. pH | pH adjustment |
| Nitrogen | N/A | Protection from oxygen |
| Water for Injection | QS | solvent |

Example 3: Stability of Terlipressin Formulations

The impact of aspartic acid formulations with and without nitrogen at pH 4.5 and acetic acid formulations with and without nitrogen at pH 4.5 were assessed at 2° C.-8° C., 25° C. and 40° C. at 3 months and 4 months. The aspartic acid and acetic acid formulations were prepared by methods similar to those described in Examples 1 and 2. The results shown in Tables 6-9 below are shown in terms of % label strength (LS) for the active ingredient (terlipressin acetate), as well as the % change as compared to the day 0 (initial) time point. Table 10 shows a comparison of the % LS data presented in Tables 6-9. Percent label strength was calculated using the following formula: (mg/mL found)/(1.0 mg/mL label strength)×100%.

TABLE 6

Aspartic Acid Formulation at pH 4.5 Stability

| | 2° C.-8° C. | | 25° C. | | 40° C. | |
|---|---|---|---|---|---|---|
| Time (months) | % LS | % change | % LS | % change | % LS | % change |
| 0 | 96.95 | — | 96.95 | — | 96.95 | — |
| 3 | 96.53 | −0.42 | 95.87 | −1.08 | 94.00 | −2.95 |
| 4 | 98.34 | 1.39 | 97.38 | 0.43 | 94.30 | −2.65 |

TABLE 7

Aspartic Acid Formulation with Nitrogen at pH 4.5 Stability

| | 2° C.-8° C. | | 25° C. | | 40° C. | |
|---|---|---|---|---|---|---|
| Time (months) | % LS | % change | % LS | % change | % LS | % change |
| 0 | 97.18 | — | 97.18 | — | 97.18 | — |
| 3 | 97.54 | 0.36 | 96.97 | −0.21 | 95.04 | −2.14 |
| 4 | 99.19 | 2.01 | 98.38 | 1.20 | 95.30 | −1.88 |

TABLE 8

Acetic Acid Formulation at pH 4.5 Stability

| Time (months) | 2° C.-8° C. % LS | 2° C.-8° C. % change | 25° C. % LS | 25° C. % change | 40° C. % LS | 40° C. % change |
|---|---|---|---|---|---|---|
| 0 | 99.22 | — | 99.22 | — | 99.22 | — |
| 3 | 100.26 | 1.04 | 99.75 | 0.53 | 97.03 | −2.19 |
| 4 | 101.87 | 2.65 | 101.07 | 1.85 | 97.38 | −1.84 |

TABLE 9

Acetic Acid Formulation with Nitrogen at pH 4.5 Stability

| Time (months) | 2° C.-8° C. % LS | 2° C.-8° C. % change | 25° C. % LS | 25° C. % change | 40° C. % LS | 40° C. % change |
|---|---|---|---|---|---|---|
| 0 | 95.70 | — | 95.70 | — | 95.70 | — |
| 3 | 95.55 | −0.15 | 95.01 | −0.69 | 92.66 | −3.04 |
| 4 | 96.87 | 1.17 | 95.99 | 0.29 | 92.27 | −3.43 |

TABLE 10

Combined Terlipressin Formulation Stability Data

| | Initial | 3 Months 2° C.-8° C. | 3 Months 25° C. | 3 Months 40° C. | 4 Months 2° C.-8° C. | 4 Months 25° C. | 4 Months 40° C. |
|---|---|---|---|---|---|---|---|
| Acetic Acid pH 4.5 | 99.22% | 100.26% | 99.75% | 97.03% | 101.87% | 101.0%7 | 97.38% |
| Acetic Acid pH 4.5 + Nitrogen | 95.70% | 95.55% | 95.01% | 92.66% | 96.87% | 95.99% | 92.2%7 |
| Aspartic Acid pH 4.5 | 96.95% | 96.53% | 95.87% | 94.00% | 98.34% | 97.38% | 94.30% |
| Aspartic Acid pH 4.5 + Nitrogen | 97.18% | 97.54% | 96.97% | 95.04% | 99.19% | 98.38% | 95.30% |

There was a clear trend that demonstrated acceptable assay values throughout the study, even at the 4 month timepoint at 40° C. (stability specification to be 90.0-110.0% label strength).

Example 4: Purity of Terlipressin Formulations

The terlipressin and aspartic acid formulations at pH 4.5 (with and without nitrogen preservation) and the terlipressin and acetic acid formulations at pH 4.5 (with and without nitrogen preservation) were tested for overall purity by HPLC after 3 months and 4 months at 2° C.-8° C., 25° C. and 40° C. The aspartic acid and acetic acid formulations were prepared by methods similar to those described in Examples 1 and 2. The overall purity results at 3 months are shown in Table 11 and the overall purity results at 4 months are shown in Table 12 with the % change values shown with respect to the initial time points. The purity/impurity data further demonstrates the stability of the product at both room temperature (i.e., 25° C.) and accelerated temperatures (i.e., 40° C.).

TABLE 11

Overall Purity of Terlipressin Formulations at 3 Months

| | Initial % Purity | 2° C.-8° C. % Purity | 2° C.-8° C. % change | 25° C. % Purity | 25° C. % change | 40° C. % Purity | 40° C. % change |
|---|---|---|---|---|---|---|---|
| Acetic Acid pH 4.5 | 98.878 | 99.258 | 0.38 | 98.890 | 0.01 | 97.107 | −1.77 |
| Aspartic Acid pH 4.5 | 99.096 | 99.247 | 0.15 | 98.754 | −0.34 | 97.051 | −2.05 |
| Acetic Acid pH 4.5 + Nitrogen | 98.245 | 98.895 | 0.65 | 98.229 | −0.02 | 96.961 | −1.28 |
| Aspartic Acid pH 4.5 + Nitrogen | 98.758 | 99.279 | 0.52 | 98.551 | −0.21 | 97.098 | −1.66 |

TABLE 12

Overall Purity of Terlipressin Formulations at 4 Months

| | Initial % Purity | 2° C.-8° C. % Purity | 2° C.-8° C. % change | 25° C. % Purity | 25° C. % change | 40° C. % Purity | 40° C. % change |
|---|---|---|---|---|---|---|---|
| Acetic Acid pH 4.5 | 98.878 | 99.344 | +0.47 | 98.988 | +0.11 | 96.542 | −2.34 |
| Aspartic Acid pH 4.5 | 99.096 | 99.389 | +0.29 | 98.854 | −0.24 | 96.408 | −2.71 |
| Acetic Acid pH 4.5 + Nitrogen | 98.245 | 98.902 | +0.66 | 98.534 | +0.29 | 96.188 | −2.09 |
| Aspartic Acid pH 4.5 + Nitrogen | 98.758 | 99.357 | +0.60 | 98.855 | +0.10 | 96.895 | −1.89 |

Figure 2:
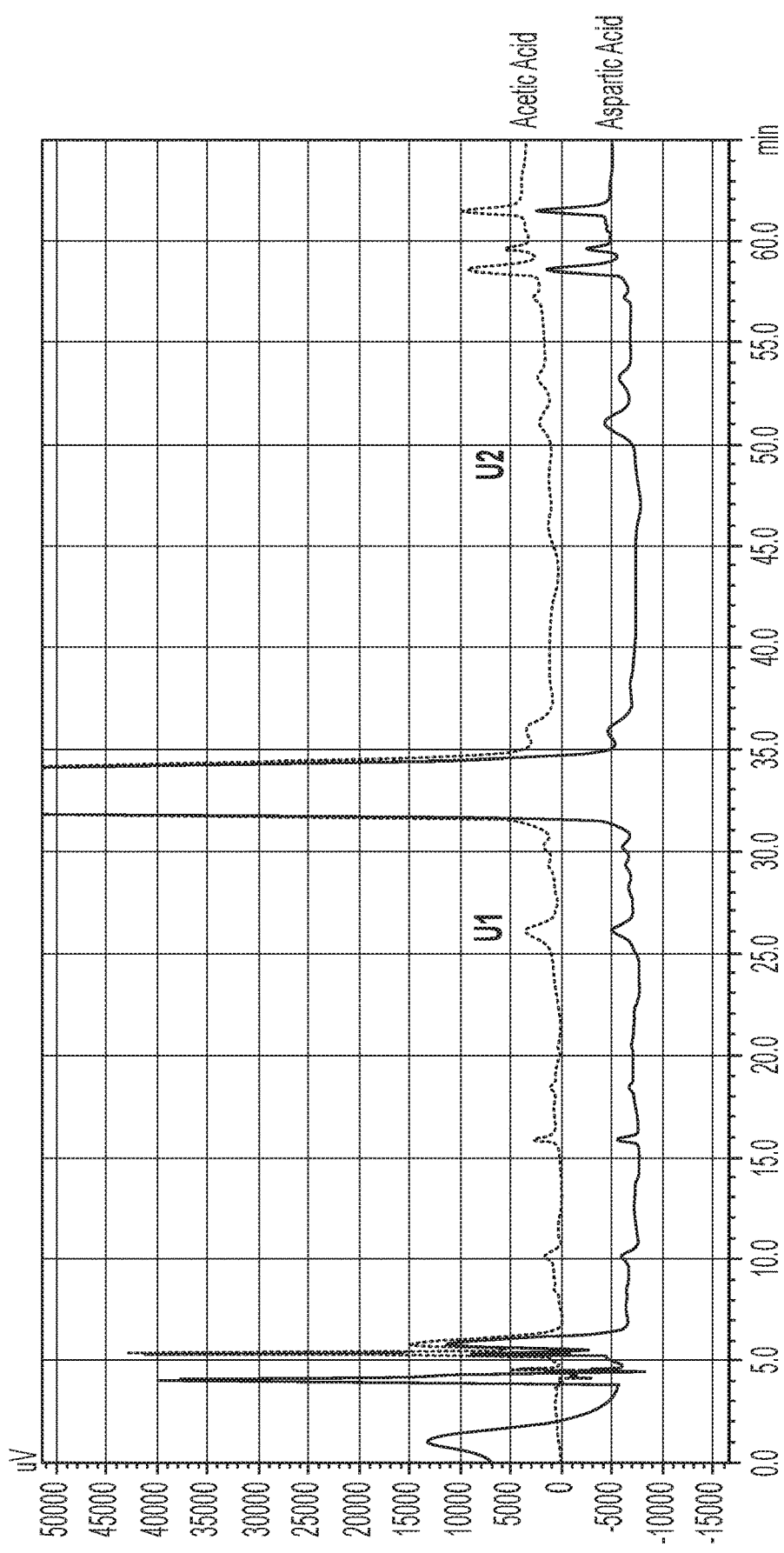
FIG. 2 is overlapping HPLC chromatograms for acetic acid and aspartic acid terlipressin formulations (without nitrogen protection) at pH 4.5 for three months at 25° C. Peaks U1 and U2 are impurities.
Figure 3:
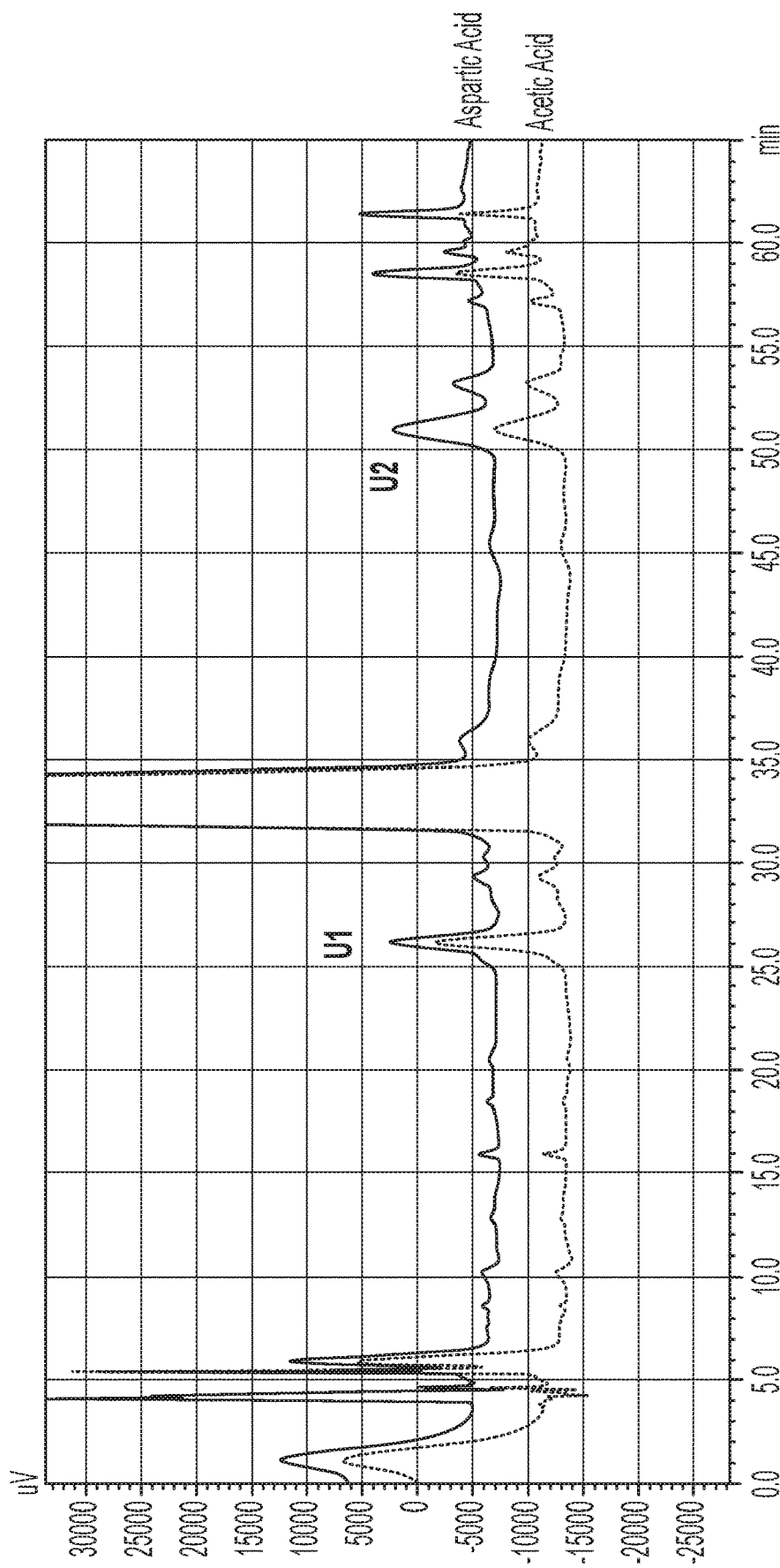
FIG. 3 is overlapping HPLC chromatograms for acetic acid and aspartic acid terlipressin formulations at pH 4.5 (without nitrogen protection) for three months at 40° C. Peaks U1 and U2 are impurities.
Figure 4:
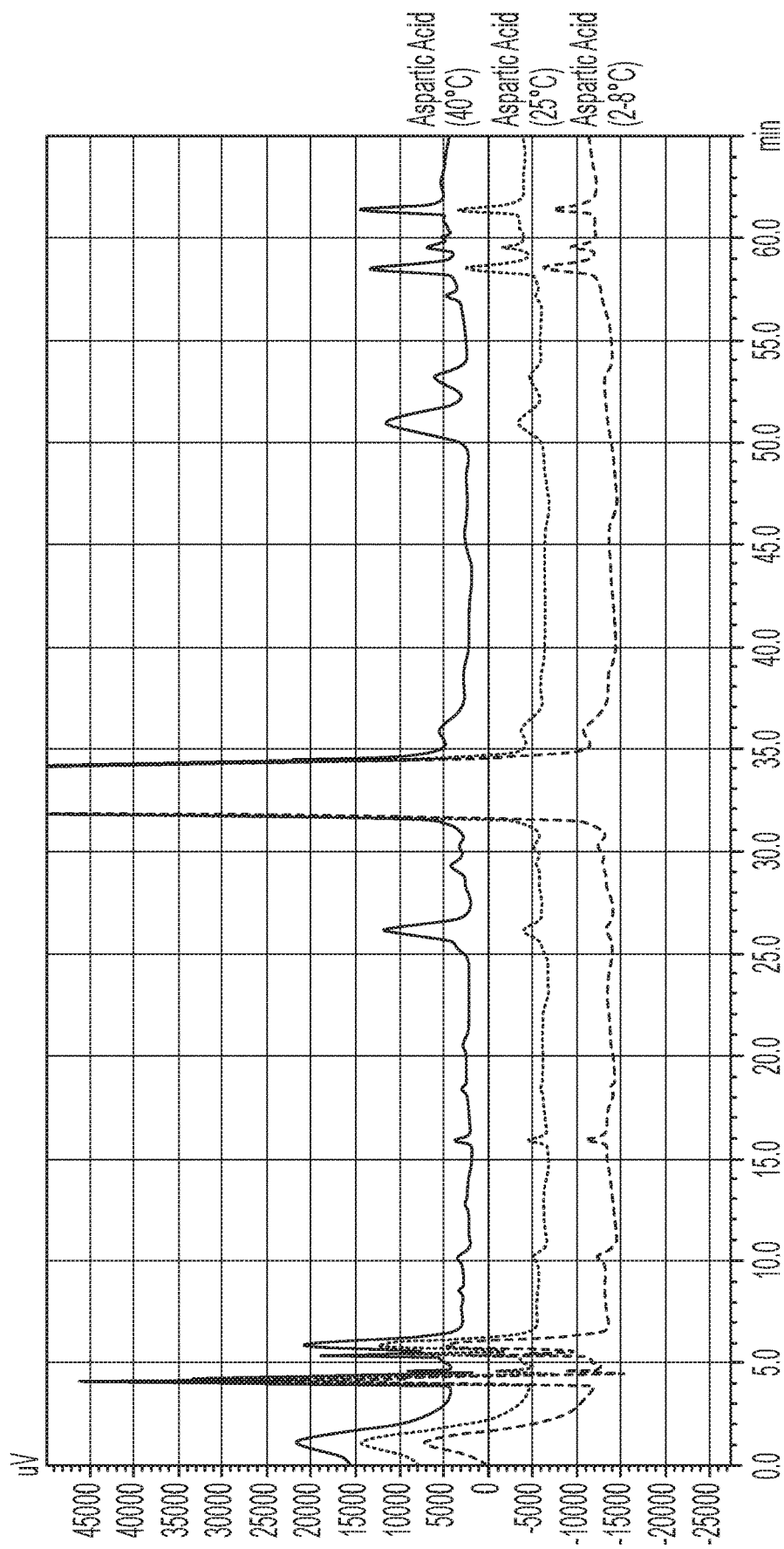
FIG. 4 is overlapping HPLC chromatograms showing temperature effects on the aspartic acid terlipressin formulation at pH 4.5 (without nitrogen protection) for three months at 2° C.-8° C., 25° C., and 40° C.
Figure 5:
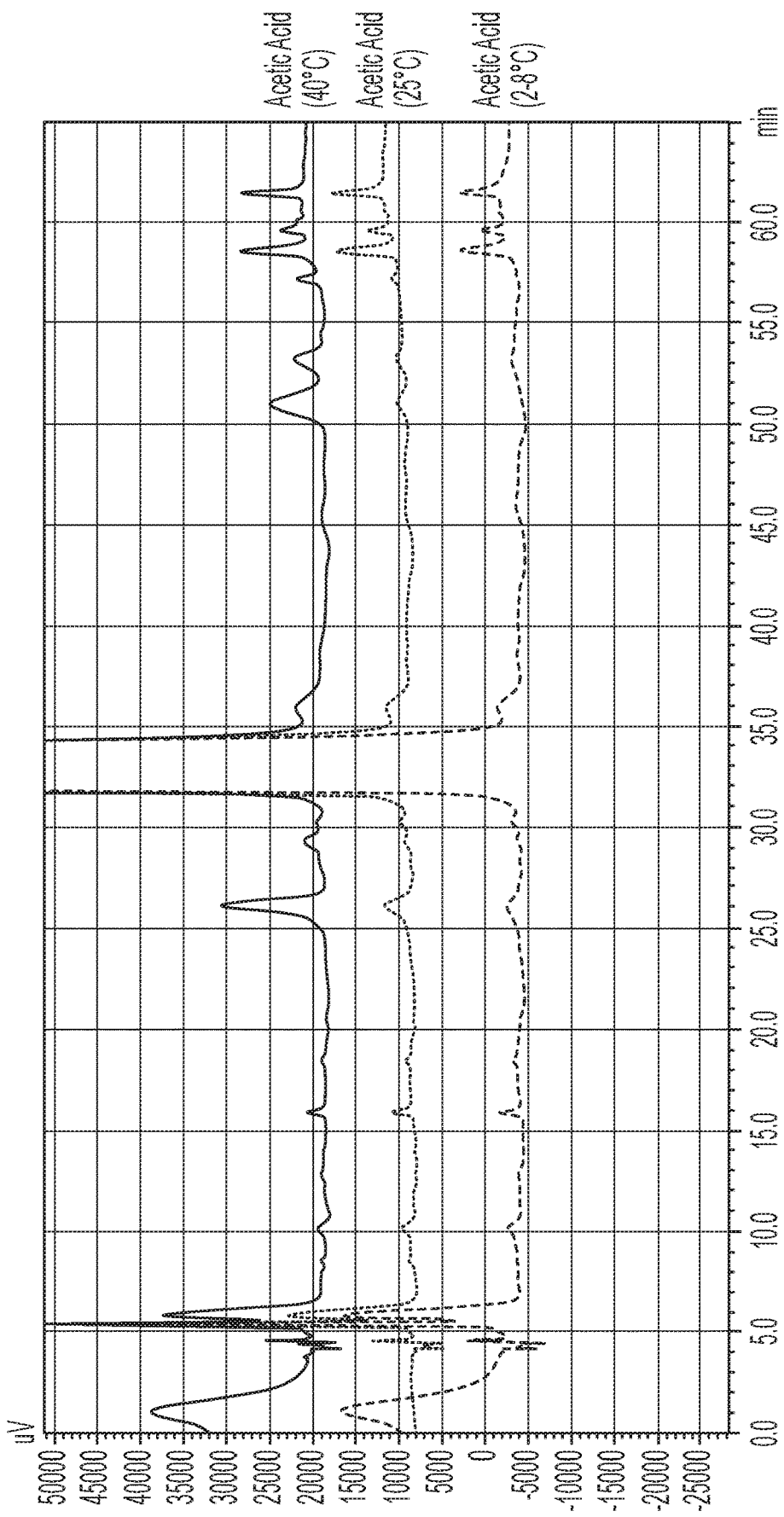
FIG. 5 is overlapping HPLC chromatograms showing temperature effects on the acetic acid terlipressin formulation at pH 4.5 (without nitrogen protection) for three months at 2° C.-8° C., 25° C., and 40° C.

Furthermore, FIGS. 1-5 are chromatograms showing the effect at three months of temperature (2° C.-8° C., 25° C., and 40° C.) of the acetic acid and aspartic acid terlipressin formulations without nitrogen at pH 4.5. FIG. 1 is overlapping HPLC chromatograms for acetic acid and aspartic acid terlipressin formulations (without nitrogen protection) at pH 4.5 for three months at 2° C.-8° C. FIG. 2 is overlapping HPLC chromatograms for acetic acid and aspartic acid terlipressin formulations (without nitrogen protection) at pH 4.5 for three months at 25° C. Peaks U1 and U2 are impurities. FIG. 3 is overlapping HPLC chromatograms for acetic acid and aspartic acid terlipressin formulations at pH 4.5 (without nitrogen protection) for three months at 40° C. Peaks U1 and U2 are impurities. FIG. 4 is overlapping HPLC chromatograms showing temperature effects on the aspartic acid terlipressin formulation at pH 4.5 (without nitrogen protection) for three months at 2° C.-8° C., 25° C., and 40° C. FIG. 5 is overlapping HPLC chromatograms showing temperature effects on the acetic acid terlipressin formulation at pH 4.5 (without nitrogen protection) for three months at 2° C.-8° C., 25° C., and 40° C.

Example 5: Long-term Stability and Purity of Terlipressin

The stability and purity of an aspartic acid terlipressin formulation with nitrogen at pH 4.4 contained in a 3 mL long glass syringe with a flurocoated plunger was assessed in a 6 month study. This formulation was prepared essentially as described in Example 1 with nitrogen overlay during filling, no nitrogen during formulation). The storage stability of the formulation was analyzed at four time points (initial [0 months], 1 month, 3 months, and 6 months) at four temperatures (5° C., 25° C., 30° C., and 40° C.). The results shown in Table 13 contain the % label strength (% LS) for the active ingredient (terlipressin acetate), the sum of impurities of the total weight of the impurities and terlipressin in the composition (% Total Impur.), and the physical appearance ("PA") of the formulation. The pH of the formulation was 4.4 at 0, 1 and 3 months (results not available for 6 months).

TABLE 13

Long Term Stability and Purity of Aspartic Acid Terlipressin Formulations at pH 4.4

| | 5° C. | | | 25° C. | | | 30° C. | | | 40° C. | | |
|---|---|---|---|---|---|---|---|---|---|---|---|---|
| Time (mo.) | LS % | Total Impur. % | PA | LS % | Total Impur. % | PA | LS % | Total Impur. % | PA | LS % | Total Impur. % | PA |
| 0 | 99.4 | 1.0 | CCS | 99.4 | 1.0 | CCS | 99.4 | 1.0 | CCS | 99.4 | 1.0 | CCS |
| 1 | 98.1 | 1.1 | CCS | 98.4 | 1.2 | CCS | 97.2 | 1.2 | CCS | 97.1 | 1.8 | CCS |
| 3 | 101.9 | 1.0 | CCS | 100.6 | 1.2 | CCS | 100.3 | 1.4 | CCS | 98.1 | 2.9 | CCS |
| 6 | 97.0 | 1.0 | CCS | 95.7 | 1.5 | CCS | 96.6 | 2.0 | NA | 87.7 | 5.5 | CCS |

PA = Physical Appearance
CCS = clear, colorless solution

The lot of API used for the manufacturing was the same for all conditions. At the time of manufacture, the batches with aspartic acid showed better purity than the ones containing acetic acid. Impurity U1 appears to be a hydrolytic product of terlipressin. The purity of the formulations containing aspartic acid after three months both at 2° C.-8° C. and 25° C. were similar to the ones containing acetic acid because of a higher increase of impurity U2.

The acetic acid formulation exhibited higher impurity profiles for a peak that is likely to be des-1,2-glycine terlipressin and the aspartic acid formulation produces higher levels of two impurities that are likely enantiomers of terlipressin. Formulations containing higher terlipressin enantiomers are preferred to having higher hydrolytic products because hydrolytic products may have much higher potency than terlipressin. Indeed, enantiomer impurities are acceptable and can be found in the US drug products for vasopressin at 6-7%. The results also indicate that the acetic acid formulations seem to degrade quicker during compounding and then degrade more slowly over time. With the rates of degradation observed in the current study, impurities of approximately 1.2% per year at 25° C. and a steady situation with no (or very minor increase) at 2° C.-8° C. can be anticipated.

As shown in Table 13, the terlipressin formulation maintained an acceptable label strength after 6 months at all temperatures except at accelerate condition 40° C. The formulation met specifications at the intermediate storage temperature (30° C.) reflecting that it is expected that the formulation will remain stable for 12-24 months or more at room temperature. The physical appearance of the formulation remained a clear, colorless solution at 6 months at all temperatures, indicating both stability and purity.

Analytical Methods

The analytical methods used in this Example 5 are from the European Pharmacopeia for analysis of terlipressin acetate API. It consists of a gradient system with two mobile phases. Accordingly, the following parameters were used: Column: Waters Symmetry C18 3.0×150 mm 5.0 µm; Wavelength: 210 nm; Flow Rate: 0.6 mL/min; Column Oven: 30° C.; Autosampler temp: 5° C.; Injection Volume: 100 µL; Run Time: 75 min; Mobile phase: Gradient; Buffer: 0.02% Sulfuric Acid in 5 mM Ammonium Sulfate in water; 1.0 mL sulfuric acid; Eluent A: Methanol: Buffer (18.5:81.5 v/v); Eluent B: Methanol:Buffer (30:70 v/v). The gradient conditions are shown in Table 1.

TABLE 1

| Gradient Conditions | | |
| --- | --- | --- |
| Gradient: Time (min) | % Eluent A | % Eluent B |
| 0 | 100 | 0 |
| 35 | 100 | 0 |
| 55 | 0 | 100 |
| 65 | 0 | 100 |
| 65.01 | 100 | 0 |
| 70 | 100 | 0 |

Any patents or publications mentioned in this specification are herein incorporated by reference to the same extent as if each individual publication was specifically and individually indicated to be incorporated by reference.

No limitation of the scope of the disclosure is intended by use herein of specific embodiments and specific language to describe the various aspects of the invention. Alteration and modification of the disclosure as illustrated herein is contemplated as would normally occur to one skilled in the art to which the disclosure relates.

Unless otherwise defined, all terms (including technical and scientific terms) used herein have the same meaning as commonly understood by one having ordinary skill in the art to which this disclosure belongs. It will be further understood that terms, such as those defined in commonly used dictionaries, should be interpreted as having a meaning that is consistent with their meaning in the context of the relevant art and the disclosure and will not be interpreted in an idealized or overly formal sense unless expressly so defined herein.

It will be further understood that a number of aspects and embodiments are disclosed. Each of these has individual benefit and each can also be used in conjunction with one or more, or in some cases all, of the other disclosed aspects and embodiments, whether specifically delineated or not. Accordingly, for the sake of clarity, this description refrains from repeating every possible combination of the individual aspects and embodiments in an unnecessary fashion. Nevertheless, the specification and claims should be read with the understanding that such combinations are implicitly disclosed, and are entirely within the scope of the disclosure and the claims, unless otherwise specified.

One skilled in the art will readily appreciate that the disclosure is well adapted to carry out the objects and obtain the ends and advantages mentioned, as well as those inherent therein. The examples along with the methods described herein are representative of preferred embodiments, are exemplary, and are not intended as limitations on the scope of the disclosure. Changes therein and other uses will occur to those skilled in the art which are encompassed within the spirit of the disclosure as defined by the scope of the claims.

The invention claimed is:

1. An aqueous composition comprising terlipressin acetate or a pharmaceutically acceptable salt thereof, wherein the composition comprises from about 0.5 to about 1.0 mg/mL terlipressin acetate or a pharmaceutically acceptable salt thereof and aspartic acid in an amount of about 0.1 to 1 mg/mL, wherein the pH of the composition is from about 3.4 to about 5.0, and wherein the composition has a sum of impurities of less than 5.0% of the total weight of the impurities and terlipressin in the composition.

2. The composition of claim 1, wherein the composition has a sum of impurities of less than 4.5% of the total weight of the impurities and terlipressin in the composition.

3. The composition of claim 1, wherein the pH of the composition is in the range of 4.0 to 5.0.

4. The composition of claim 1, wherein the composition is stable at about 25° C. for at least 24 months and at 30° C. and about 75% relative humidity for at least six months.

5. The composition of claim 1, wherein the composition is stable at about 30° C. to about 40° C. and about 75% relative humidity for up to 26 weeks.

6. The composition of claim 1, wherein the composition is stable at about 25° C. and about 60% relative humidity for up to 2 years.

7. The composition of claim 1, wherein the composition is stored at 2°° C. to 8° C.

8. The composition of claim 1, wherein the composition comprises an isotonicity agent.

9. The composition of claim 8, wherein the isotonicity agent is, dextrose or sodium chloride.

10. The composition of claim 1, wherein the composition comprises a pH adjusting agent.

11. The composition of claim 1, wherein the pH adjusting agent is hydrochloric acid, potassium hydroxide, acetic acid, sodium hydroxide, or potassium hydroxide.

12. A prefilled syringe comprising the composition of claim 1.

13. A kit comprising the composition of claim 1, wherein the kit comprises a container for the composition, wherein the container optionally has a means for injecting the composition into a subject.

14. The kit of claim 13, wherein the container is a syringe that is pre-filled with the composition.

15. The kit of claim 13, wherein the kit further comprises a needle and/or a syringe rod.

16. The kit of claim 13, wherein the kit further comprises instructions for administering the composition, wherein the instructions provide administering the composition by continuous infusion or as a bolus intravenous dose.

17. The kit of claim 16, wherein the continuous infusion is administered with an ambulatory pump or other controlled delivery device.

18. The kit of claim 16, wherein the instructions provide the option of administering the composition by injecting the composition into a container of diluent that can then be connected to or inserted into an ambulatory pump for continuous infusion.

* * * * *